(12) United States Patent
Garcia

(10) Patent No.: US 11,517,396 B2
(45) Date of Patent: Dec. 6, 2022

(54) RETRACTABLE GEAR MESHING JOINT AND ARM

(71) Applicant: Zimmer Biomet CMF and Thoracic, LLC, Jacksonville, FL (US)

(72) Inventor: Saddy Garcia, St. Augustine, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 470 days.

(21) Appl. No.: 16/802,166

(22) Filed: Feb. 26, 2020

(65) Prior Publication Data
US 2020/0268477 A1 Aug. 27, 2020

Related U.S. Application Data

(60) Provisional application No. 62/811,278, filed on Feb. 27, 2019.

(51) Int. Cl.
*A61B 90/50* (2016.01)
*F16H 1/04* (2006.01)
*F16H 61/36* (2006.01)
*F16H 63/30* (2006.01)

(52) U.S. Cl.
CPC ............... *A61B 90/50* (2016.02); *F16H 1/04* (2013.01); *F16H 61/36* (2013.01); *A61B 2560/06* (2013.01); *F16H 2063/3093* (2013.01)

(58) Field of Classification Search
CPC ............... A61B 90/50; A61B 2560/06; A61B 2090/508; F16H 1/04; F16H 61/36; F16H 2063/3093
See application file for complete search history.

(56) References Cited

U.S. PATENT DOCUMENTS

| 10,072,793 | B2 | 9/2018 | Wyslucha et al. |
| 10,562,453 | B2* | 2/2020 | van Stiphout ........... B60R 1/074 |
| 2014/0208514 | A1* | 7/2014 | Schuerch, Jr. ...... A61G 13/1245 29/428 |
| 2015/0297305 | A1 | 10/2015 | Wyslucha et al. |
| 2015/0374362 | A1 | 12/2015 | Gettinger et al. |
| 2019/0184551 | A1* | 6/2019 | Shafer ....................... B25J 9/126 |
| 2020/0268477 | A1* | 8/2020 | Garcia ..................... F16H 61/36 |

FOREIGN PATENT DOCUMENTS

| DE | 10132358 | 1/2003 |
| DE | 102011004370 | 8/2012 |
| WO | 2020176651 | 9/2020 |

OTHER PUBLICATIONS

"International Application Serial No. PCT/US2020/019940, International Search Report dated Jun. 19, 2020", 4 pgs.
"International Application Serial No. PCT/US2020/019940, Written Opinion dated Jun. 19, 2020", 6 pgs.
"International Application Serial No. PCT/US2020/019940, International Preliminary Report on Patentability dated Sep. 10, 2021", 8 pgs.

* cited by examiner

*Primary Examiner* — Victor L MacArthur
(74) *Attorney, Agent, or Firm* — Schwegman Lundberg & Woessner, P.A.

(57) ABSTRACT

A mechanical arm assembly can include a link movable in space, an actuator, and a joint. The actuator can include a housing secured to the link and can include a cable within the housing, where the cable can be translatable relative to the housing and the link. The joint can include a main shaft, a main gear, a meshing gear, and a release plate.

24 Claims, 22 Drawing Sheets

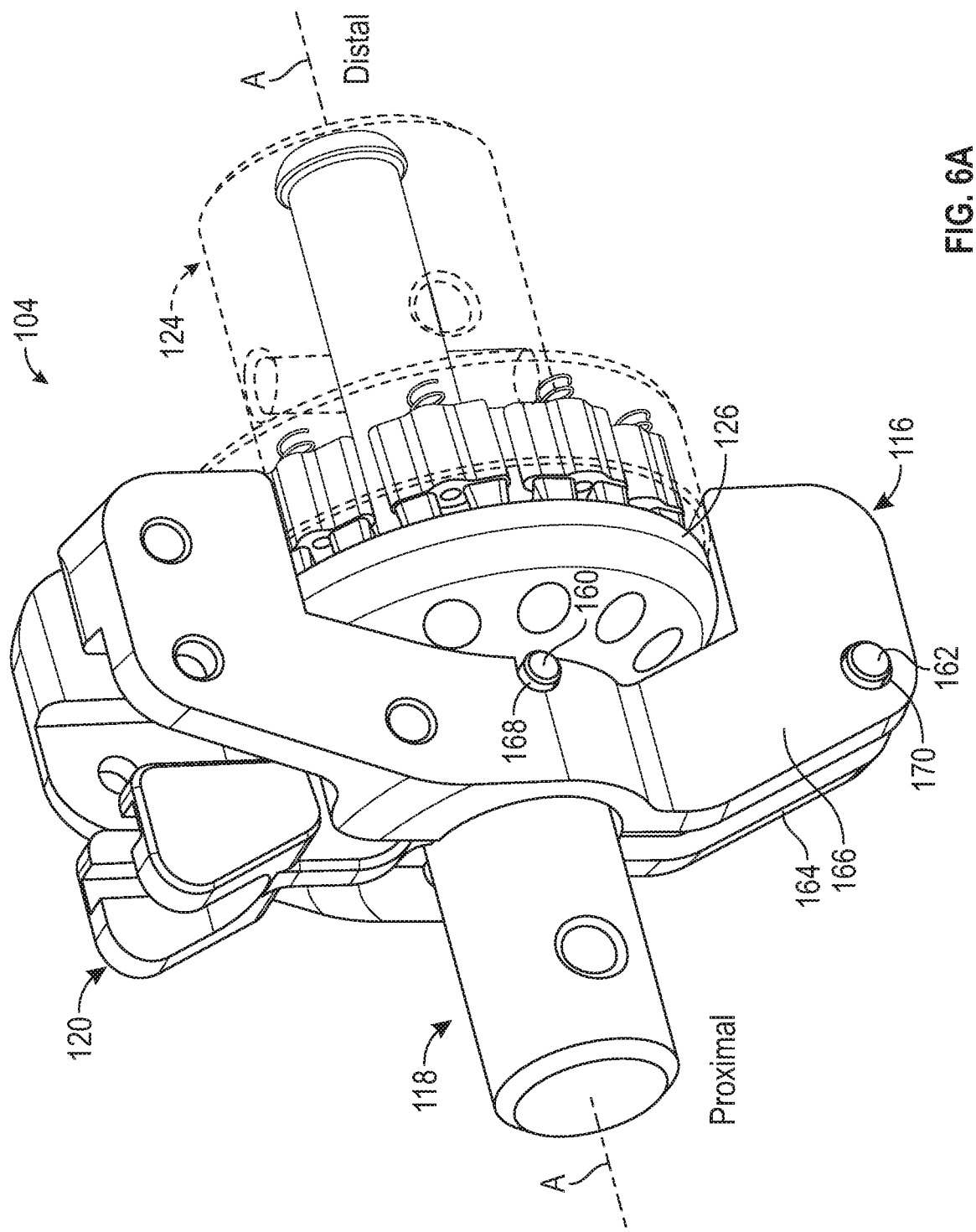

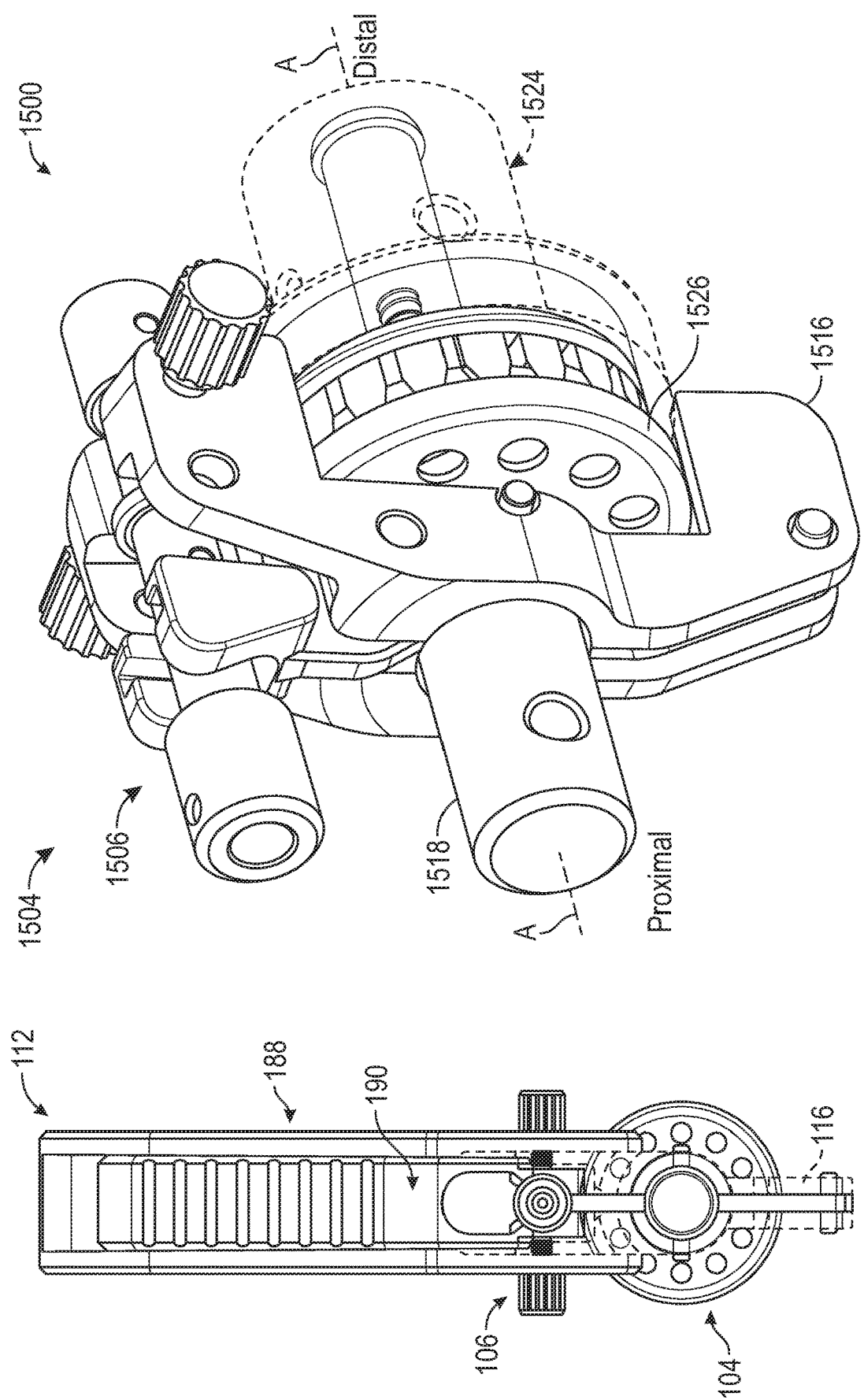

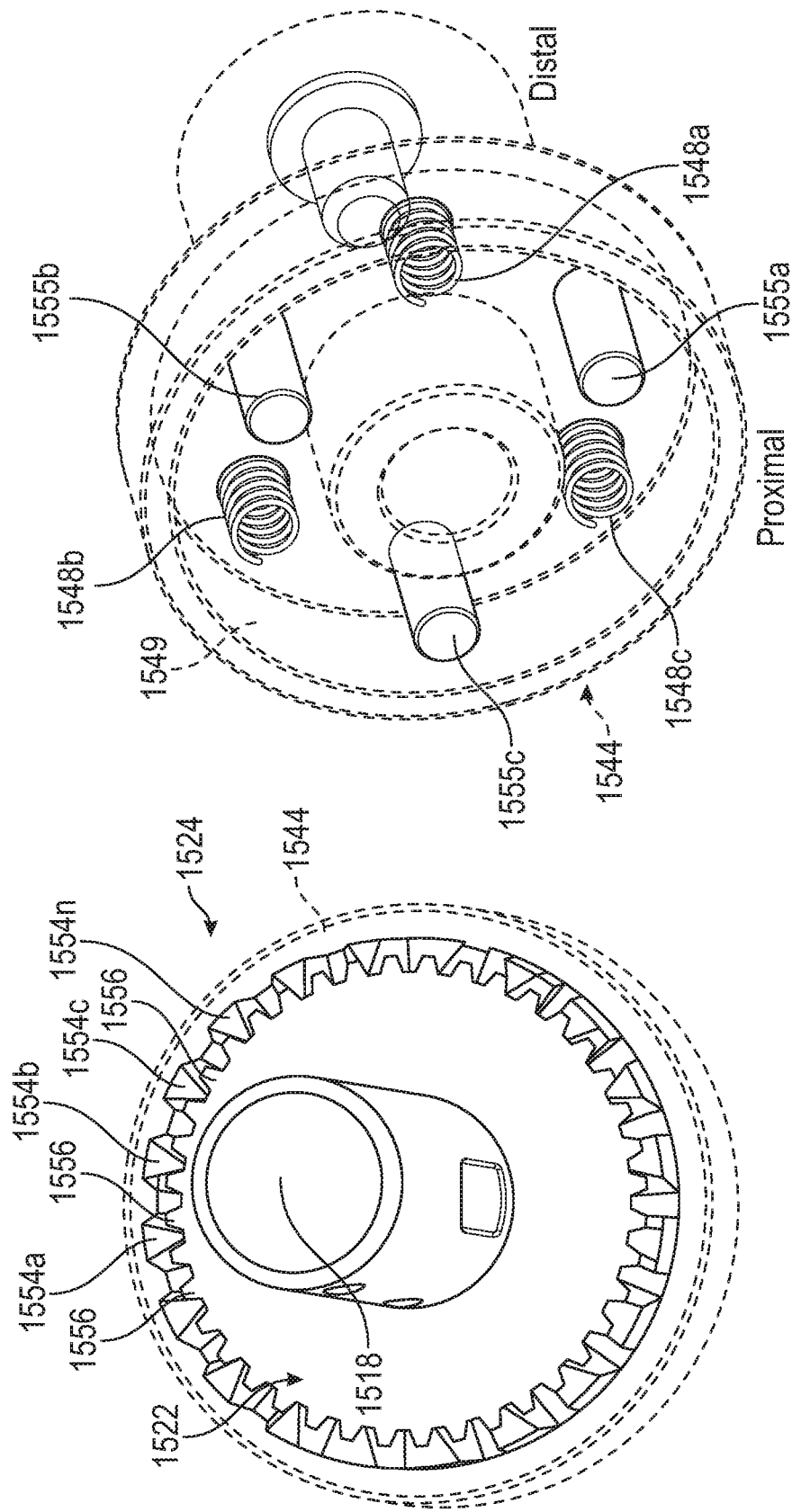

RETRACTABLE GEAR MESHING JOINT AND ARM

CLAIM OF PRIORITY

This application claims the benefit of U.S. Provisional Patent Application Ser. No. 62/811,278, filed on Feb. 27, 2019, the benefit of priority of which is claimed hereby, and which is incorporated by reference herein in its entirety.

CROSS-REFERENCE TO RELATED PATENT DOCUMENTS

This patent application is also related to Saddy Garcia., U.S. Non-Provisional Patent application Ser. No. 15/918, 531 entitled "End Effector Coupler For Surgical Arm," filed on Mar. 12, 2018 which is hereby incorporated by reference herein in its entirety.

BACKGROUND

The present invention relates generally to apparatus and systems for supporting surgical and other tools. Some surgical procedures include use of a variety of tools. In some of these procedures, it is required that tools, such as a retractor, be maintained in a single position for an extended period of time, such as an hour or more. During this time, other tools can be used to perform other aspects of the surgery. Because it may be difficult or undesirable to manually hold a position of a tool for such lengths of time, mechanical and/or electromechanical arms can be used to hold the position of the tool while other aspects of the procedure are performed, in other procedures, it may be required to support a limb (such as an arm or a leg) of a patient during a procedure. Some mechanical arms can be adjustable such that a position of the arm can be adjusted before or during the procedure to support a tool or limb.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6A shows an isometric view of a portion of a joint of a surgical arm assembly, in accordance with an example of the present disclosure.

FIG. 14C shows a sideview of a joint of a surgical arm assembly, in accordance with an example of the present disclosure.

FIG. 15 shows an isometric view of a joint of a surgical arm assembly, in accordance with an example of the present disclosure.

FIG. 17A shows an isometric view of a portion of a joint of a surgical arm assembly, in accordance with an example of the present disclosure.

FIG. 17B shows an isometric view of a portion of a joint of a surgical arm assembly, in accordance with an example of the present disclosure.

DETAILED DESCRIPTION

Some surgical procedures require a variety of tools. In some cases, it is desired to hold took, such as a retractor, in a single position for an extended period of time, such as an hour or more. In these procedures, adjustable mechanical and/or electromechanical arms are often used to hold the position of the tool while other aspects of the procedure are performed. In other procedures, mechanical arms are used to support limbs of patients (such as an arm or a leg) for prolonged procedures such as joint replacement or fracture repair.

One type of mechanical arm sometimes employed is an arm that is manually articulable when unlocked and is prevented from being moved when locked. Often, modern surgical procedures require a high degree of precision and accuracy. As a result, it is desirable to position a surgical tool supported by surgical arm as precisely and accurately as possible. Further, it is desirable to use the same arm to support limbs of patients when necessary, requiring joints of the arm to be strong enough to support the load of a limb in any position.

This disclosure helps to provide accurate tool positioning through the use of an articulating surgical arm including joints having a high resolution or a high angular precision. In each of the joints momentary rotational action and restriction can be used to position a distal end of the arm at a desired point in space relative to a support to which the arm can be fixed. The joints can include a set of gears engageable to lock the joint which can transfer relatively high loads between links of the arm for support of limbs.

The joints can be operated to disengage the gears from each other to allow movement of the links or components connected to the joints. In some examples, a meshing gear can include one or more sets of teeth biased to engage a main gear to lock the joint. A release of the joint can be operated to translate the teeth to disengage the main gear from the meshing gear to allow relative movement of the main gear and the meshing gear (and of the components connected thereto). In some examples, sets of teeth of the meshing gear can be offset relative to each other such that only a portion of the sets of teeth engage the main gear in any relative position of the main gear to the meshing gear. The angular offset of the sets of teeth can allow for the meshing gear to engage the main gear with a relatively high resolution or angular precision (such as half a degree or one degree increment of adjustment), helping to provide accurate and precise placement of the tool coupled to the arm. Also, by providing a mechanical gear, the arm can be operated without the use of electrical power. As the arm is articulated, the joints can rotate independently of each other such that the joints can rotate at different degrees or increments of rotation relative to each other to allow for the arm to be position as desired.

Figure 1:
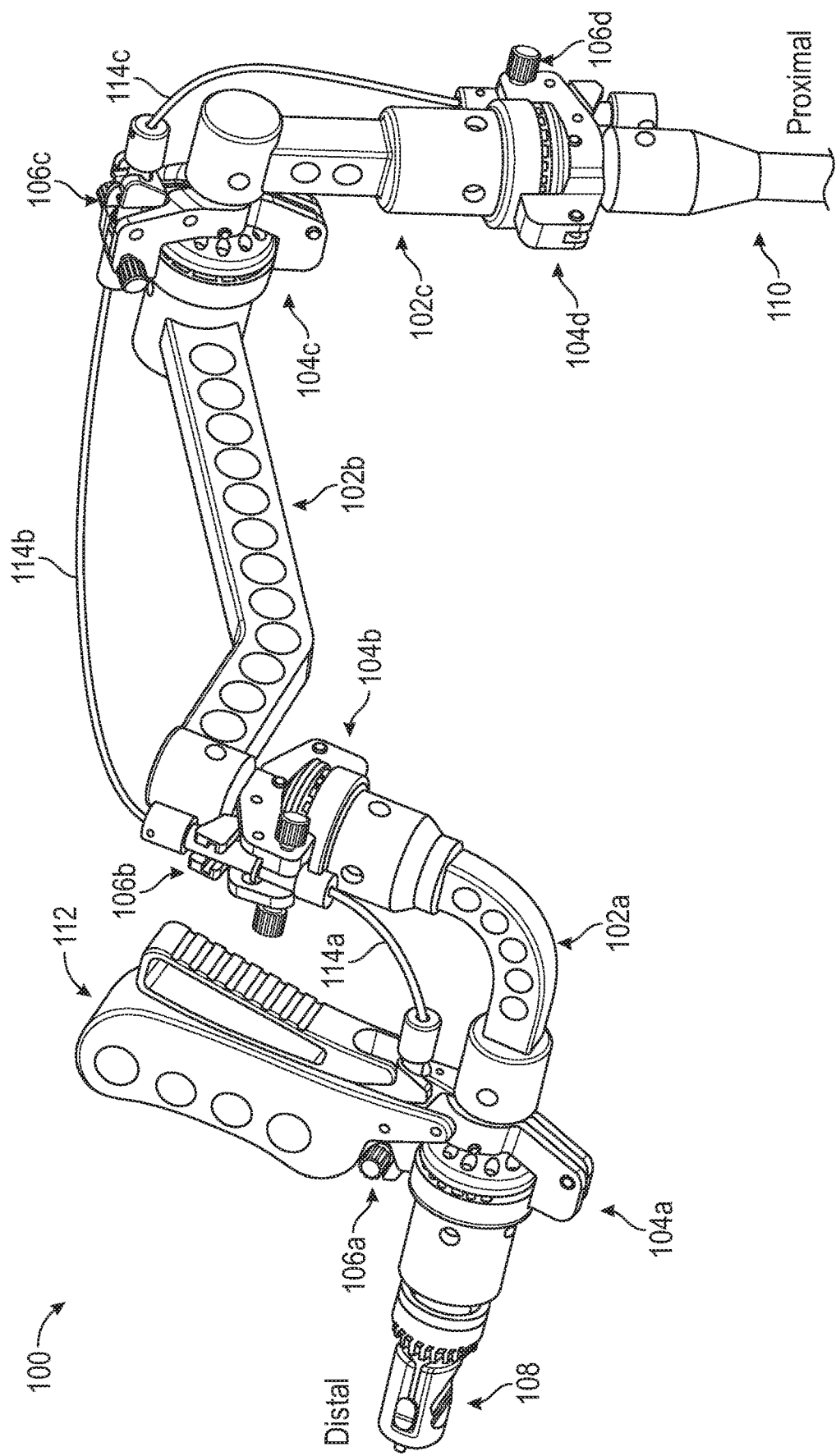
FIG. 1 shows an isometric view of a surgical arm assembly, in accordance with an example of the present disclosure.

FIG. 1 shows an isometric view of a mechanical arm assembly 100, in accordance with an example of the present disclosure. The mechanical arm assembly 100 can be a mechanical articulable surgical arm that can include one or more joints operable or actuatable to enable independent movement of the links for positioning a tool supported by the arm.

The mechanical arm assembly 100 can include links 102a, 102b, and 102c (collectively referred to as the links 102), joints 104a, 104b, 104c, and 104d, (collectively referred to as the joints 104), actuators 106a., 106b, 106c, and 106d (collectively referred to as the actuators 106), a tool or coupler 108, a support 110, a handle assembly 112, and cables 114a, 114b, and 114c (collectively referred to as the cables 114). Also shown in FIG. 1 are orientation indicators Proximal and Distal.

Each of the links 102a, 102b, and 102c can be a rigid or semi-rigid body comprised of materials such as metals, plastics, foams, elastomers, ceramics, composites, or combinations thereof. The links 102 can each include proximal and distal portions couplable to other components, such as the joints 104.

Each of the joints 104a, 104b, 104c, and 104d, can be mechanical components including one or more gears, as discussed below in further detail. Each of the joints 104 can be coupled to one of the links 102, the support 110, or the tool 108 at one side and can be coupled to another component at an opposite side. For example: the joint 104a can be connected to the tool 108 at a distal side of joint 104a and to the link 102a at a proximal side of joint 104a; the joint 104b can be connected to the link 102a at a first (or distal) side of the joint 104b and can be connected to the link 102b at a second (or proximal) side of the joint 104b; the joint 104c can be connected to the link 102b at a proximal side of the joint 104c and can be connected to the link 102c at a distal side of the joint 104c; and, the joint 104d can be connected to the link 102c at a first side of the joint 104d and can be connected to the support 110 at a second side of the joint 104d. In this way, the joints 104 can connect the tool 108 to the support 110 via the links 102.

Each of the actuators 106a, 106b, 106c, and 106d can be actuators movable in response to movement or translation of an inner cable of the cables 114. The actuators 106 can include two components connected to opposing parts of one of the joints 104. For example, a first part of the actuator 106a can connect to a housing of the joint 104a and a second part of the actuator 106a can connect to a release of the joint 104. Each of the actuators 106 can be connected to one or more cables. For example: the actuator 106a can be connected to the cable 114a; the actuator 106b can be connected to the cables 114a and 114b; the actuator 106c can be connected to the cables 114b and 114c; and, the actuator 106d can be connected to the cable 114d.

The tool 108 can be a surgical tool or a coupler securable to a distal portion of the mechanical arm 100. The tool 108 can be an end effector coupler, a driver, a clamp, a forceps, a cutting tool, or the like. The support 110 can be a rigid or semi-rigid member configured to support the mechanical arm 100. The support 110 can be connected to an operating table or a movable or stationary support frame. In other examples, the tool 108 can be replaced by a device configured to support limbs, such as a sling, pad, or the like.

The handle assembly 112 can be can be a rigid or semi-rigid member comprised of materials such as metals, plastics, foams, elastomers, ceramics, composites, or combinations thereof. The handle assembly 112 can be sized and shaped to be grasped and actuated or operated. The handle assembly 112 can be connected or coupled to any of the joints 104 and actuators 106, such as the joint 104a and the actuator 106.

Each of the cables 114a, 114b, and 114c (collectively referred to as the cables 114) can be flexible cables including an outer housing and an internal cable movable within and relative to the outer housing. In some examples, the cables 114 can be Bowden cables or the like and can be disposable or reprocessed following a procedure. For example, the cables 114 can be reprocessed with or separate from the mechanical arm assembly 100, and such processing can include removal from the support 110 and/or the mechanical arm assembly 100; cleaning and sterilization of the arm 100 and/or cables 114; and, reinstalling the arm 100 and/or cables 114 for another surgical operation.

In operation of some examples, the joints 104 can be in a locked position such that the links 102, the tool 108, and the support 110 are prevented from moving relative to each other. When it is desired to change a position of the tool 108, the handle assembly 112 can be pressed or operated by a user to actuate the actuator 106a. Because the actuator 106a is connected to a release of the joint 106, actuation of the actuator 106a can cause the release to unlock the joint 106, allowing the link 102a to move relative to the tool 108. Also, because the actuator 106a is connected to the cables 114 and remainder of the actuators 106, operation of the handle assembly 112 can also cause the actuators 106b, 106c, and 106d to respectively unlock joints 104b, 104c, and 104d. When each of the joints 114 is unlocked, each of the tool 108 and the individual links 102a, 102b, and 102c can be moved individually for movement of the tool 108 in space and with respect to the support 110.

While the joints 104 are unlocked, the handle assembly 112 can also be used to move the components of the mechanical arm 100 to position the tool 108 (and/or other components of the mechanical arm 100) at a desired location. When a desired position of the tool 108 is achieved (or when it is otherwise desired to lock the joints 104), the handle assembly 112 can be released allowing the joints 104 to re-lock as the joints 104 can be biased to a locked position.

Such operations of the mechanical arm 100 could be useful for soft tissue retraction, holding of medical instruments, or limb holding, for example. Also, the mechanical arm 100 could be used in other industries for holding instruments or work pieces in a desired orientation while helping to provide access and clearance around the mechanical arm 100 while working. Further details of components and operations of the mechanical arm 100 are discussed below.

Figure 2A:
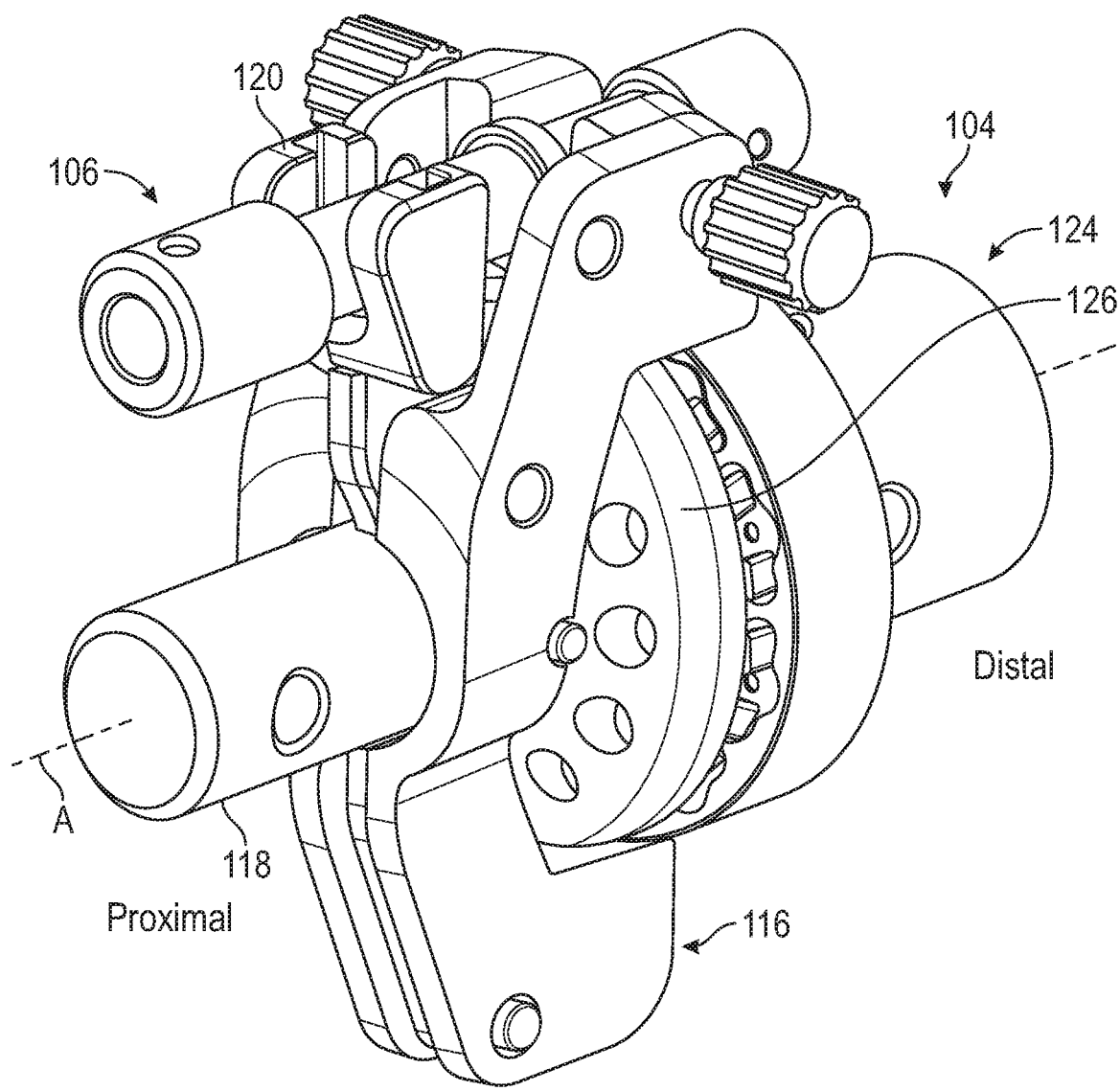
FIG. 2A shows an isometric view of a joint of a surgical arm assembly, in accordance with an example of the present disclosure.
Figure 2B:
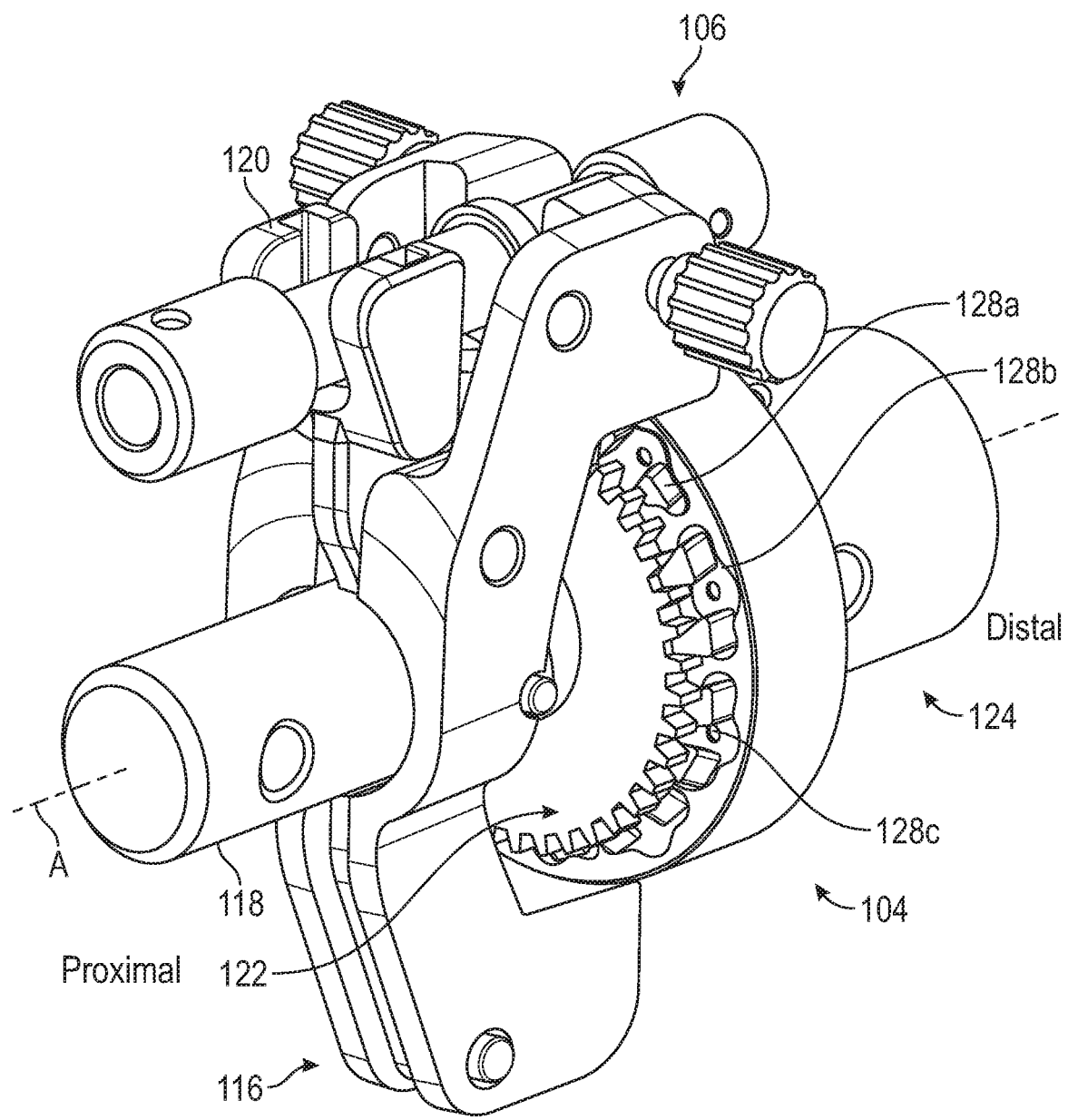
FIG. 2B shows an isometric view of a joint of a surgical arm assembly, in accordance with an example of the present disclosure.

FIG. 2A shows an isometric view of the joint 104 and the actuator 106 of the mechanical arm assembly 100, in accordance with an example of the present disclosure. FIG. 2B shows an isometric view of the joint 104 and the actuator 106 of the mechanical arm assembly 100, in accordance with an example of the present disclosure. Release plate 126 is removed in FIG. 2B for clarity. FIGS. 2A and 2B are discussed below concurrently.

The joint 104 and the actuator 106 of the mechanical arm assembly 100 can be consistent with FIG. 1; further details of the joint 104 and the actuator 106 are discussed with respect to FIGS. 2A and 2B. For example, joint 204 can include a bracket 116, a main shaft 118, a release 120, a main gear 122, a meshing gear 124, a release plate 126, and tooth sets 128a, 128b, and 128c. Also shown in FIGS. 2A and 2B are axis A and orientation indicators Proximal and Distal.

The bracket 116 (or handle housing) can be a rigid or semi-rigid body comprised of materials such as metals, plastics, foams, elastomers, ceramics, composites, or combinations thereof. The bracket 116 can include two components couplable to the main shaft 118 while allowing the main shaft 118 to extend through the bracket 116, as discussed in further detail below. The bracket 116 can be sized and shaped to surround the main gear 122, the meshing gear 124, and the release plate 126 on a distal side of the bracket 116. The bracket 116 can also be connectable to the release 120, which can extend partially between the bracket 116. The bracket 116 can also be configured to connect to the actuator 106.

The main shaft 118 can be a rigid or semi-rigid body comprised of materials such as metals, plastics, foams, elastomers, ceramics, composites, or combinations thereof. The main shaft 118 can extend along axis A and can be configured to support the main gear 122, the meshing gear 124, and the release plate 126 thereon. In some examples, the bracket 116 and/or the release 120 can be connected to the main shaft 118.

The release 120 can be a rigid or semi-rigid member and can be couplable to the main shaft 118 and the bracket 116. The release 120 can also be coupled to the actuator 106 and engageable with the release plate 126. The actuator 106 can be secured to the bracket 116 such that movement of the actuator 106 relative to the bracket 116 is limited and movement of the actuator 106 causes movement of the release 120.

The main gear 122 can be a rigid or semi-rigid gear supported by and coaxial with the main shaft 118. In some examples, the main gear 122 can be coupled to the main shaft 118 so that the main gear 122 rotates with the main shaft 118. in some examples, the main shaft 118 and the main gear 122 can be monolithically formed. The main gear 122 can be a spur gear, a helical gear, a screw gear, a bevel gear, or the like. In some examples, the main gear 122 can be an external spur gear, that is, a spur gear having teeth extending radially outward from a body of the gear.

The meshing gear 124 can be a rigid or semi-rigid gear supported by and coaxial with the main shaft 118. In some examples, the meshing gear 124 can be coupled to the main shaft 118 such that the meshing gear 124 can rotate independently of the main shaft 118 when the meshing gear 124 is not engaged with the main gear 122. The meshing gear can be a spur gear, a helical gear, a screw gear, a bevel gear, or the like. In some examples, the meshing gear 124 can be an internal spur gear, that is, a spur gear having teeth extending radially inward from a body of the gear. The meshing gear 124 can include a body and a plurality of tooth sets 128a, 128b, and 128c. Each tooth set 128 can be located within its own bore of the meshing gear body and can be biased to extend proximally from the body, as discussed in further detail below.

The release plate 126 can be a rigid or semi-rigid plate or body supported by the main shaft 118 and coaxial therewith. The release plate 126 can extend radially outward from the main shaft 118 and can be translatable relative to the main shaft 118. In some examples, the release plate 126 can have a geometric shape of an open cylinder sized to surround the main gear 122. A distal portion of the release plate 126 can have a distal face configured to engage the tooth sets 128. Because the joint 104 can be comprised of substantially rigid mechanical components, the joint 104 can be substantially entirely autoclavable and sterilizable.

In operation of some examples, one or more tooth sets 128 can be engaged with teeth of the main gear 122 to connect the main gear 122 to the meshing gear 124 when the release 120 and actuator 106 are in locked positions. In such a configuration, the main shaft 118 is configured to rotate with the meshing gear 124 allowing forces to be transferred between components connected to the main shaft 118 and to the meshing gear 124. When it is desired to move the meshing gear 124 (and/or a component connected thereto, such as a link) relative to the main gear 122 and the main shaft 118 (and/or a component connected thereto such as another link), the actuator 106 can be operated to translate distally. Because the actuator 106 is secured to the bracket 116, movement of the actuator 106 causes distal movement of the release 120. Distal movement of the release 120 can cause engagement of the release 120 with the release plate 126, which can translate relative to the main shaft 118 distally to engage the tooth sets 128. Such engagement can cause the tooth sets 128 to move distally into bores of the meshing gear 124 so the tooth sets 128 disengage the main gear 122, which can separate the main gear 122 from the meshing gear 124. When the main gear 122 is disengaged from the meshing gear 124, the main gear 122 and the main shaft 118 can rotate relative to the meshing gear 124 (and any component connected thereto).

When a desired relative angular position of the main gear 122 with respect to the meshing gear 124 is achieved, the actuator 106 (which is connected to the handle assembly 112) can be moved proximally, which can allow the release plate 126 to be moved proximally along the main shaft 118 to disengage the tooth sets 128. Because the tooth sets 128 can be biased to a proximal position, the tooth sets 128 can help move the release plate 126 to a proximal position and the tooth sets 128 can move proximally to reengage the teeth of the main gear 122, thus re-locking the meshing gear 124 to the main gear 122 to limit rotation of the meshing gear 124 relative to the main gear 122 and the main shaft 118. Such a locking and unlocking process can be repeated as desired.

Because the meshing gear 124 can mesh with the main gear 122, a relatively large torque or rotational force can be transferred through the joint 104 allowing the arm 100 to be used for limb support and to support heavy tool loads. Further, because the joint does not require a battery, motor, or electrical components, production of electrical interference on other tools can be reduced.

In some examples, the actuator 106 can be omitted from the assembly and the joint 104 can be operated by hand. For example, when the actuator 106 is omitted, the release 120 can be moved to a proximal position to lock the main gear 122 to the meshing gear 124 and the release 120 can be moved to a distal position to unlock the main gear 122 from the meshing gear 124.

Figure 3A:
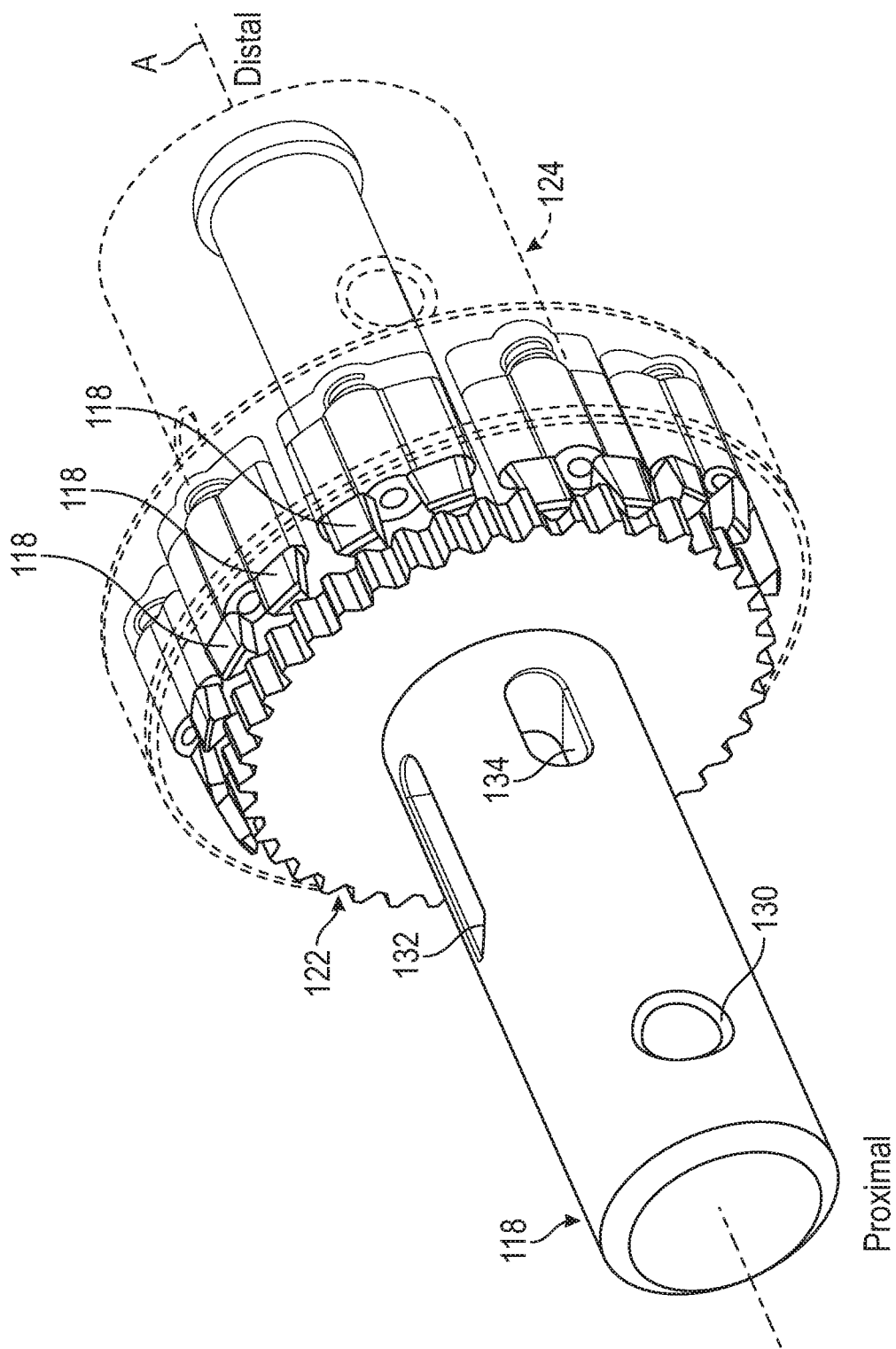
FIG. 3A shows an isometric view of a portion of a joint of a surgical arm assembly, in accordance with an example of the present disclosure.
Figure 3B:
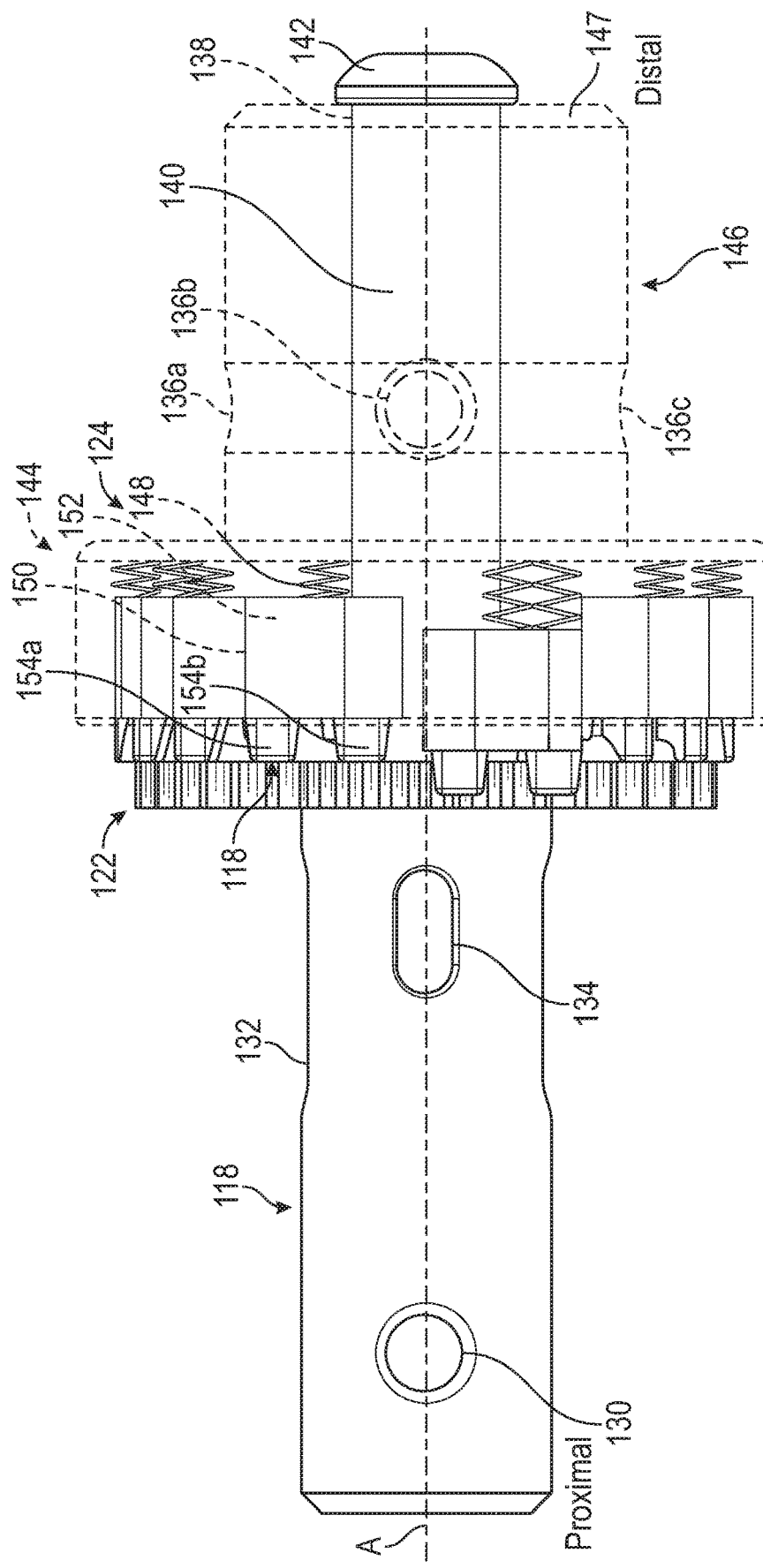
FIG. 3B shows a side view of a portion of a joint of a surgical arm assembly, in accordance with an example of the present disclosure.

FIG. 3A shows an isometric view of a portion of the joint 104 of a surgical arm assembly, in accordance with an example of the present disclosure. FIG. 3B shows a side view of a portion of the joint 104 of a surgical arm assembly, in accordance with an example of the present disclosure. FIGS. 3A and 3B are discussed below concurrently. Shown in FIGS. 3A and 3B are axis A and orientation indicators Proximal and Distal.

The joint 104 of FIGS. 3A and 3B can be consistent with FIGS. 1-2B discussed above; FIGS. 3A and 3B show additional details of the joint 104, For example, FIGS. 3A and 3B show a component bore 130, a release slot 132, and a pin slot 134.

The component bore 130 can be a bore extending through the main shaft 118 near a proximal end of the main shaft 118 and substantially orthogonal to the axis A. The component bore 130 can be configured to receive a fastener (such as a bolt, screw, pin, or the like) therethrough, so as to secure a component to the main shaft 118. In some examples, the component bore 130 can be threaded.

The release slot 132 can be a slot or channel (or in some examples a bore) extending through the main shaft 118 near the main gear 122 and substantially orthogonal to the axis A. The release slot 132 can be configured to receive the release 120 (shown in FIGS. 2A and 2B) therethrough to position the release 120 adjacent to (and/or in contact with) the release plate 126. The release slot 132 can be larger than the release 120 to allow the release 120 to translate a relatively short axial distance relative to the main shaft 118.

The pin slot 134 can be a slot, channel, bore, or the like extending through the main shaft 118 substantially orthogonal to the axis A and substantially orthogonal the release slot 132. The pin slot 134 can intersect the release slot 132 such that the pin slot 134 can receive a fastener (such as a pin) therethrough to pass through the release 120 to secure the release 120 to the main shaft 118.

FIGS. 3A and 3B also show meshing gear bores 136a, 136b, and 136c (collectively referred to as meshing gear bores 136), a shaft bore 138, an extension 140, and a fastener 142.

The meshing gear bores 136 can be bores extending into a distal body portion 146 of the meshing gear 124. Each of the meshing gear bores 136 can be configured to receive one or more fasteners or components to secure a component or tool to the meshing gear 124. The meshing gear bores 136 can be smooth, threaded, or the like.

The shaft bore 138 can be a bore extending through the meshing gear 124 and can be configured to receive an extension 140 of the main shaft 118 therethrough and/or fastener 142 therethrough. The extension 140 can be a portion of the main shaft 118 extending distally from the main gear 12.2 where the extension 140 can have a relatively smaller diameter than a proximal portion of the main shaft 118.

The fastener 142 can be a pin, bolt, screw, or the like configured to engage with the extension 140 to secure the distal body portion 146 to the main shaft 118. The fastener 142 can be securable to the extension 140 of the main shaft 118 to engage an outer (distal) surface 147 of the meshing gear 124 to retain the meshing gear 124 while allowing rotation of the meshing gear 124 relative to the main shaft 118 and the main gear 122.

FIGS. 3A and 3B also show tooth bores 150, which can be bores extending into a proximal body portion 144 of the meshing gear 124. The proximal body portion 144 can be coupled to the distal body portion 146 of the meshing gear where the proximal body portion 144 has a relatively larger diameter. The tooth bores 150 can extend from a proximal surface of the proximal body portion 144 of the meshing gear into the proximal body portion 144 and can terminate therein.

The tooth bores 150 can be sized to receive both a body 152 and a first tooth 154a and a second tooth 154b of the tooth set 118 therein. The tooth bores 150 can each be sized to receive a biasing element 148 and a tooth set 118 therein where the biasing element 148 can contact a distal end of the proximal body portion 144 within the tooth bores 150 and can contact a distal portion of the body 152 to bias the teeth 154a and 154b of the tooth set 118 to extend proximally from the proximal body portion 144.

Figure 4:
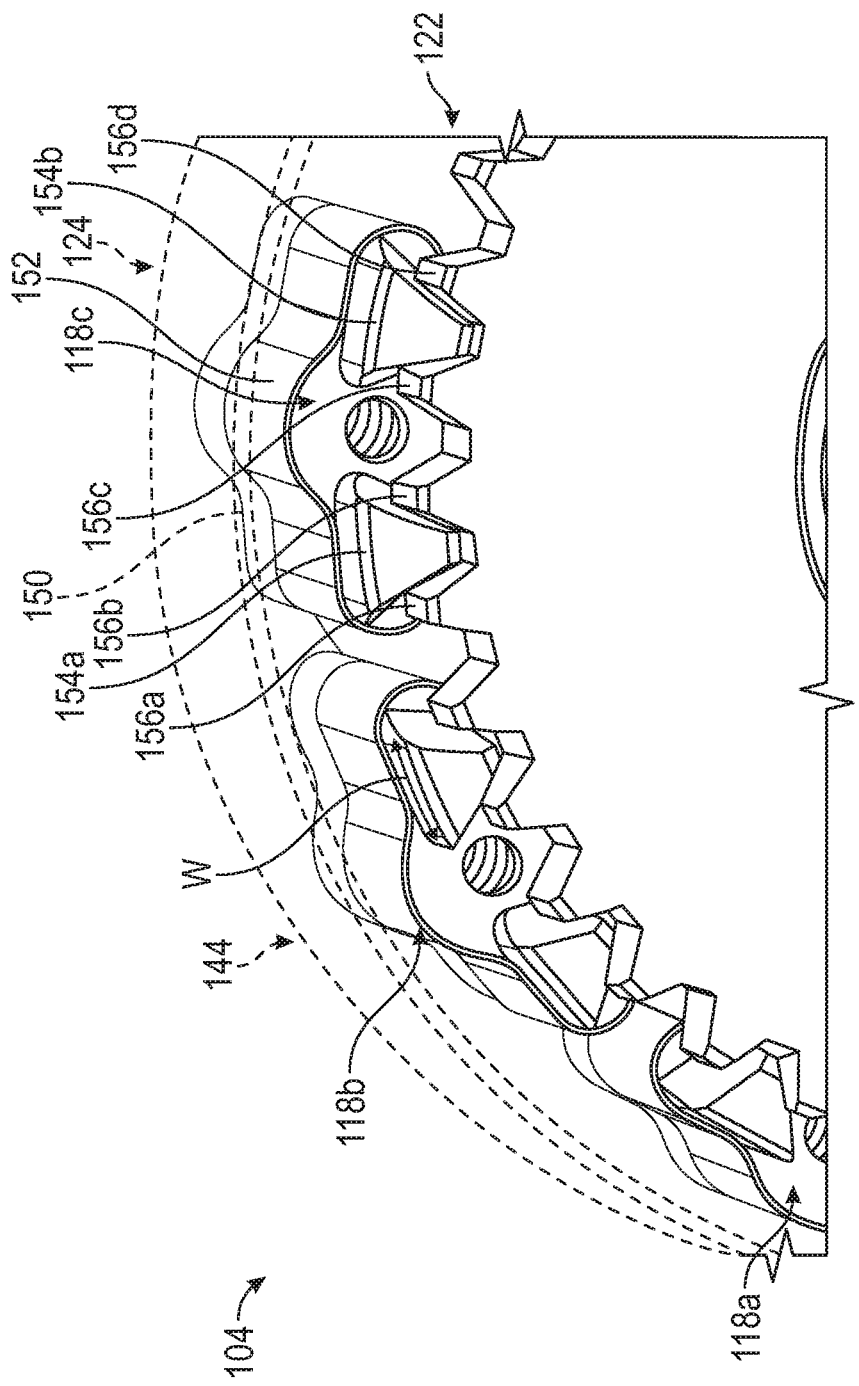
FIG. 4 shows a focused isometric view of a portion of a joint of a surgical arm assembly, in accordance with an example of the present disclosure.

FIG. 4 shows a focused isometric view of a portion of the joint 104 of a surgical arm assembly, in accordance with an example of the present disclosure. The joint 104 of FIG. 4 can be consistent with FIGS. 1-3B discussed above; FIG. 4 shows additional details of the joint 104.

FIG. 4 shows how the sets of teeth 118a, 118b, and 118c can engage teeth 156 of the main gear 122 to couple or interlock the main gear 122 to the meshing gear 124. For example, tooth 154a can extend between teeth 156a and 156b or the main gear 122 and tooth 154b can extend between teeth 156c and 156d of the main gear 122 to couple the main gear 122 to the meshing gear 124 such that the main gear 122 and the meshing gear 124 interlock to rotate together.

FIG. 4 also shows how the first tooth 154a and the second tooth 154b each extend from the base 152 of the tooth set 118 such that when the base 118 is disposed in the bore 150 of the proximal body portion 144 each of the first tooth 154a and the second tooth 154b can extend away from and out of the bore 150 when the release plate is not engaging the tooth sets 118 (in the locked position). When the release plate 126 engages the tooth sets 118, the tooth sets 118 can be forced into their respective bores 150.

The first tooth 154a and the second tooth 154b can have a geometric shape of a truncated triangular pyramid and can have other shapes in other examples. The first tooth 154a and the second tooth 154b can be tapered as the first tooth 154a and the second tooth 154b extend proximally from the base 152. Each tooth set 118 can include two teeth, where the first tooth 154a is spaced apart from the second tooth 154b by a distance substantially equal to a width W of the first tooth. In other examples, the first tooth 154a can be spaced apart from the second tooth 154b at other distances, such as twice the width W, with no space between (adjacent teeth), or anywhere in between.

Figure 5:
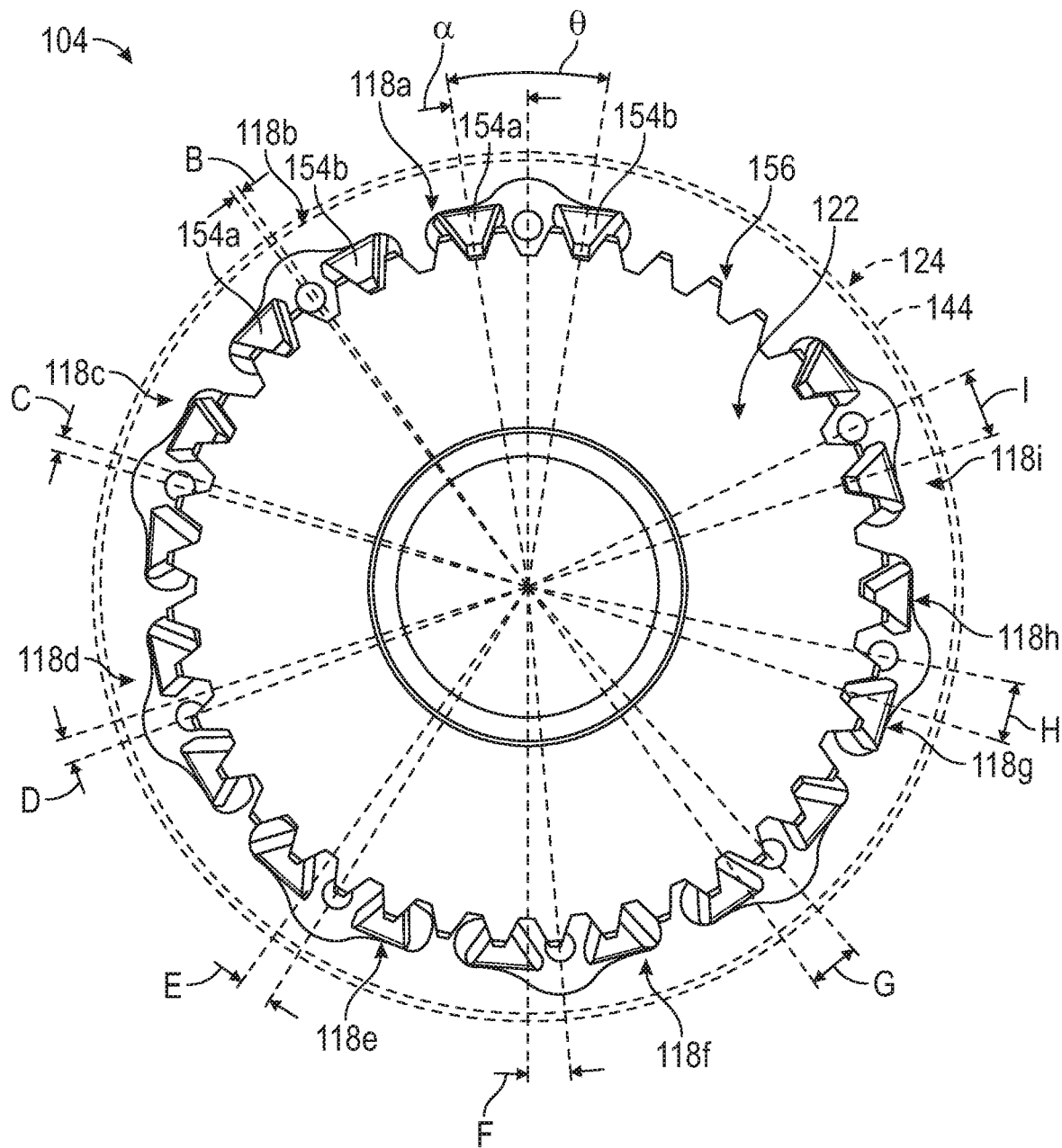
FIG. 5 shows an end view of a portion of a joint of a surgical arm assembly, in accordance with an example of the present disclosure.

FIG. 5 shows an end view of a portion of a joint 104 of a surgical arm assembly, in accordance with an example of the present disclosure. The joint 104 of FIG. 5 can be consistent with FIGS. 1-4 discussed above; FIG. 5 shows additional details of the joint.

FIG. 5 shows the main gear 122 (including main gear teeth 156) and the proximal body portion 144 of the meshing gear along with tooth sets 118a-118i each including a first tooth 154a and a second tooth 154b. FIG. 5 also shows a tooth set angle θ, and a main gear angle α. FIG. 5 further shows offset angles B, C, D, E, F, G, H, and I. By including angular offsets of the tooth sets 118a-118i, the teeth 156 of the main gear 122 can align with the teeth 154 of the meshing gear 124 at more degrees of relative rotation between the meshing gear 124 and the main gear 122. In an example where an increment of adjustment (the difference between each offset angle) is one degree, the meshing gear 124 and the main gear 122 can engage at every relative rotational position in increments of one degree of the meshing gear 124 and the main gear 122 between 0 and 360 because at least one tooth set of the meshing gear 124 will engage at least one of the main gear teeth 156 to allow for transfer of forces between the meshing gear 124 and the main gear 122. These features can allow for easier locking of the joint 104 during positioning of the mechanical arm assembly 100, and locking of the joint 104 without relative movement of components connected to either side of the joint 104, such as a tool and a link, helping to improve accuracy and repeatability of positioning the tool in space using the mechanical arm assembly 100.

By way of example, the meshing gear 124 can include nine tooth sets 118. The number of tooth sets can be determined based on the number of teeth per tooth set, the spacing of the teeth, and a desired angular precision or increment of adjustment of the meshing gear 124 with respect to the main gear 122 where the increment of adjustment is how far the main gear 122 must be rotated with respect to the meshing gear 124 before at least one of teeth 156 of the main gear 122 will align with and therefore engage the teeth 154 of the meshing gear 124.

For example, the bores of the meshing gear 124 can be circumferentially spaced with respect to the meshing gear 124 such that the first tooth 154a and the second tooth 154b are spaced from each other at the angle θ, which can be two times the angle α at which the teeth 156 of the main gear 122 are spaced, where the reference lines forming the angle θ align with both the center of the teeth 154a and 154b and the grooves or recesses between the teeth 156 of the main gear 122. That is, the angular offset between the spacing of the teeth 156 and the teeth 154 for the tooth set 118a is substantially 0 degrees as the teeth of the tooth set 118a are engaged with the teeth 156 of the main gear 122.

The third tooth 154a and the fourth tooth 154b of the tooth set 118b can also be spaced from each other at the angle θ. However, the third tooth 154a and the fourth tooth 154b of the tooth set 118b can have an angular offset of the angle B, where angle B is defined by a first reference line aligned with a groove of the main gear 122 and the second reference line is aligned with a center of the tooth set 118b (where a third tooth of the tooth set 118b) would be. That is, first tooth 154a of the tooth set 118a and the third tooth 154a of the tooth set 118b can also be spaced from each other at the second angle (the angle θ plus the angle B). Angles C-I can be similarly defined with respect to their tooth sets (118c-118i) with respect to the center of the grooves (or spaces) between the teeth 156 of the main gear 122. Also, the second tooth 154b of the tooth set 118a and the fourth tooth 154b of the tooth set 118b can be spaced from each other at a second angle (the angle θ plus the angle B) that is greater than the angle θ. When the first tooth 154a and the second tooth 154b of the tooth set 118a align with the main gear teeth 156, the third tooth 154a and the fourth tooth 154b of the tooth set 118b do not align with the main gear teeth 156. When the misalignment occurs, in some examples, the teeth of the tooth set 118b can still partially engage the teeth 156 due to the tapered shape of the teeth 154.

In some examples, angle B can be can be the minimum increment of adjustment, which can be an angle of 0.1 degrees, 0.2, 0.3, 0.4, 0.5, 1.0, 1.5, 2, 3, 4, 5 degrees, or the like. In some examples, the angle B can be selected to define a number of meshing gear teeth, where the number of meshing gear teeth is equal to or greater than (360/nMT)/i, where nMT is a number of main gear teeth and i is an increment of adjustment of the meshing gear with respect to the main gear. For example, the angle B can be the increment of adjustment (i) of one degree and nMT can be 40 such that the minimum number of meshing gear teeth is 9. That is, when the angular offset or increment of adjustment is 1 degree, 9 meshing gear teeth are required at 9 offsets to ensure that at least one meshing gear tooth will engage the teeth 156 of the main gear 122. In this example, angle B can be 1 degree, angle C can be 2 degrees, angle D can be 3 degrees, angle E can be 4 degrees, angle F can be 5 degrees, angle G can be 6 degrees, angle H can be 7 degrees, and angle I can be 8 degrees. That is, the angle B is 1 degree greater than angle α, angle C is 1 degree greater than angle B, angle D is 1 degree greater angle C, angle E is 1 degree greater than D, angle F is 1 degree greater than angle E, angle G is 1 degree greater than angle F, angle H is 1 degree greater than angle G, and angle I is 8 times that of angle B.

In operation the teeth 154 of the tooth set 118a will engage the teeth 156 when the teeth 156 are offset 0 degrees with respect to the meshing gear 124; the teeth of the tooth set 118b will engage the teeth 156 when the teeth 156 have an angular offset of 1 degree; the teeth of the tooth set 118c will engage the teeth 156 when the teeth 156 have an angular offset of 2 degrees; teeth of the tooth set 118d will engage the teeth 156 when the teeth 156 have an angular offset of 3 degree; teeth of the tooth set 118e will engage the teeth 156 when the teeth 156 have an angular offset of 4 degrees; teeth of the tooth set 118f will engage the teeth 156 when the teeth 156 have an angular offset of 5 degrees; teeth of the tooth set 118g will engage the teeth 156 when the teeth 156 have an angular offset of 6 degrees; teeth of the tooth set 118h will engage the teeth 156 when the teeth 156 have an angular offset of 7 degrees; teeth of the tooth set 118i will engage the teeth 156 when the teeth 156 have an angular offset of 8 degrees; and, teeth of the tooth set 118a will engage the teeth 156 when the teeth 156 have an angular offset of 9 degrees because 9 degrees equates to rotational movement of one full tooth of the main gear 122 with respect to the meshing gear 124.

Though the equation above can define a minimum number of teeth, more teeth per tooth set can be used. As shown in FIG. 5, two teeth can be used per tooth set to ensure at least two of the meshing gear teeth 154 engage the main gear teeth 156, which can increase force transfer between the main gear 122. and the meshing gear 124. In other examples of an increment of 1 degree with the main gear 124 having 40 teeth, 3 teeth can be provided per tooth set 118. Also, though the angular offset angles B through I are shown as increasing incrementally, the angular offsets can be placed around the main gear 122 non-incrementally as desired. Also, in an example where each tooth set 118 includes only one tooth, more tooth sets can be used. In this example, teeth of the same angular offset can be placed at different positions around the meshing gear 124 to provide engagement of two teeth at different radial positions (e.g., in different radial quadrants or on opposite sides) of the main gear 122 to help transfer forces between the main gear 122 and the meshing gear 124.

Figure 6B:
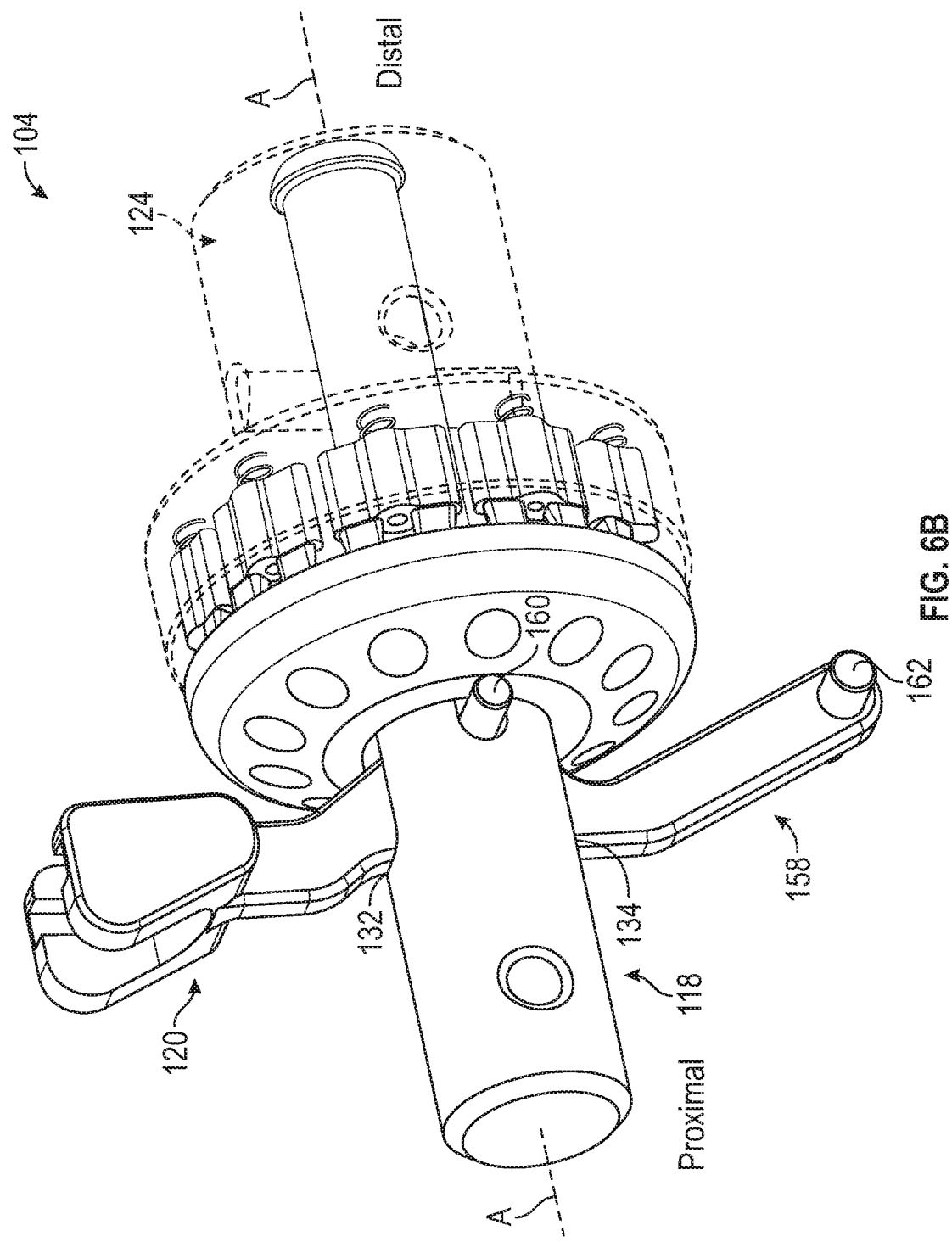
FIG. 6B shows an isometric view of a portion of a joint of a surgical arm assembly, in accordance with an example of the present disclosure.
Figure 7:
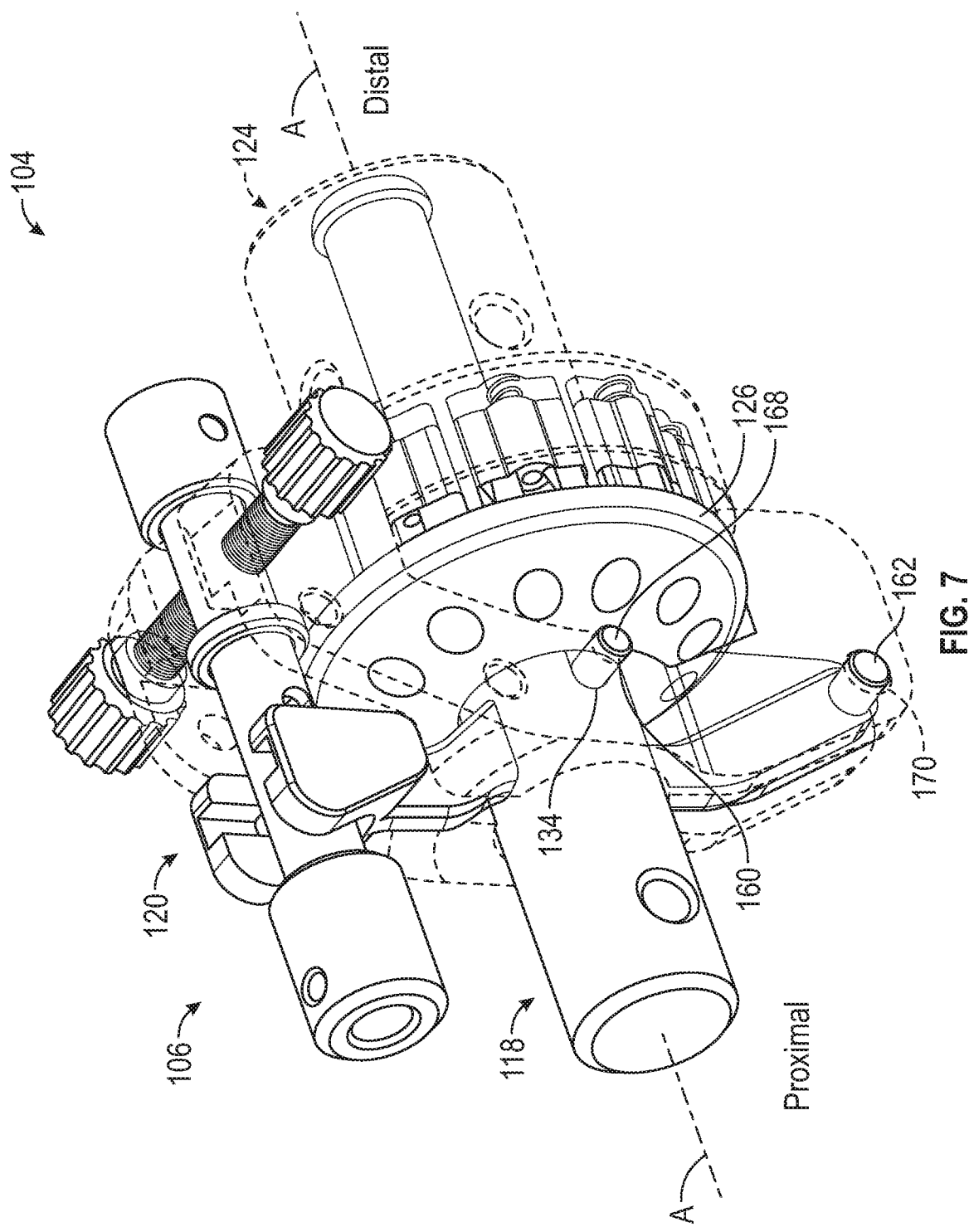
FIG. 7 shows an isometric view of a joint of a surgical arm assembly, in accordance with an example of the present disclosure.

FIG. 6A shows an isometric view of a portion of the joint 104 of a surgical arm assembly, in accordance with an example of the present disclosure. FIG. 6B shows an isometric view of a portion of the joint 104 of a surgical arm assembly, in accordance with an example of the present disclosure. FIG. 7 shows an isometric view of the joint 104 of a surgical arm assembly, in accordance with an example of the present disclosure. FIGS. 6A, 6B, and 7 are discussed below concurrently.

The joint 104 of FIGS. 6A and 6B can be consistent with the joint 104 discussed above; FIGS. 6A and 6B show further details of the joint 104 such as how release 120 can include a body 158, a shaft pin 160, and a bracket pin 162. Also, bracket 116 can include a first portion 164 and a second portion 166. The bracket 116 can also include a bracket channel 168 and a bracket bore 170. FIG. 7 shows the bracket 116 in phantom. FIGS. 6A, 6B, and 7 also show axis A and orientation indicators Proximal and Distal.

The body 158 of release 120 can be elongate and sized to extend through the release slot 132 of the main shaft 118. The shaft pin 160 can be a fastener (such as a pin, bolt, screw, or the like) configured to extend through the bracket channel 168 of the bracket 116, through the pin slot 134 of the main shaft, and through the body 158 of the release to align the release 120 with the release plate 126 where the pin slot 134 and the pin bracket channel 168 can limit movement of the release 120 with respect to the main shaft 118 and the bracket 116. The first portion 164 and the second portion 166 can surround the release 120 to retain the release 120 within in the bracket 116.

The bracket pin 162 can be a fastener (such as a pin, bolt, screw, or the like) configured to extend through the bracket bore 170 and the release body 158 to secure the release 120 to the first portion 164 and the second portion 166. Because the bracket pin 162 can secure the release 120 to the bracket 116 through the bracket bore 170, the release 120 can rotate about the bracket pin 162. Such rotation can cause a translation like movement of the release 120 with respect to the main shaft over the distance the release 120 can move as limited by the pin slot 134 to guide engagement between the release 120 and/or the pin 160 with the release plate 126 to translate the release plate 126 distally along the shaft 118.

FIG. 7 also shows actuator 106, which can be coupled to the release 120 and secured to the bracket 116, as discussed below in further detail with respect to FIGS. 8A-8C.

Figure 8A:
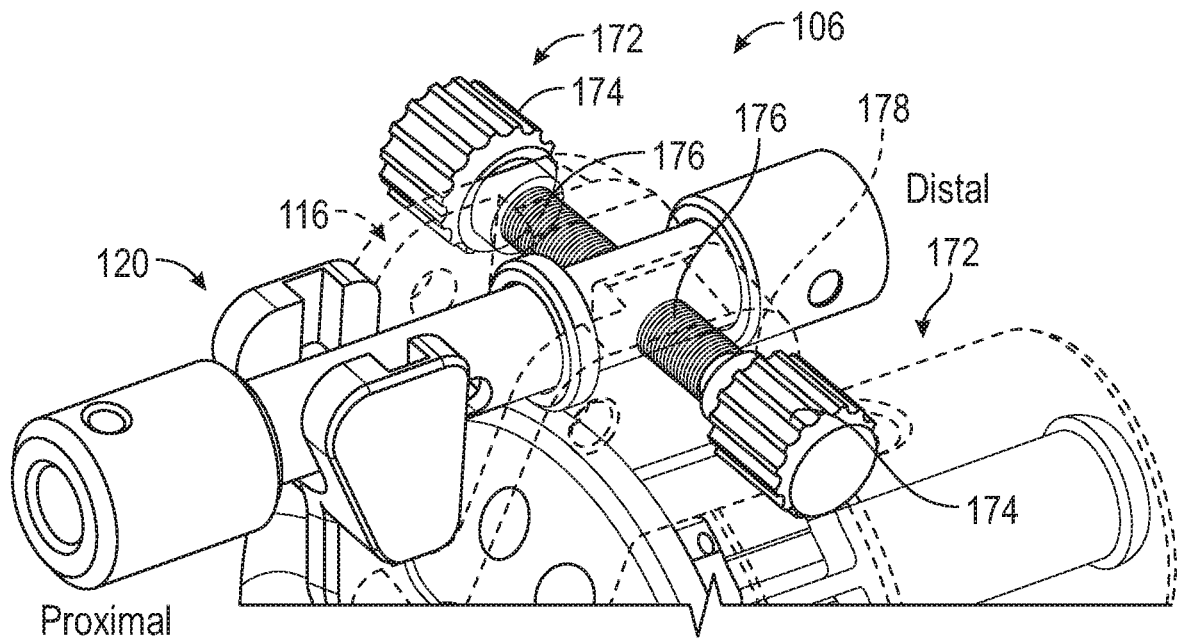
FIG. 8A shows a focused isometric view of a joint of a surgical arm assembly, in accordance with an example of the present disclosure.

FIG. 8A shows a focused isometric view of the joint 104 of a surgical arm assembly, in accordance with an example of the present disclosure. FIG. 8B shows an isometric view of the actuator 106 of a surgical arm assembly, in accordance with an example of the present disclosure. FIG. 8C shows an isometric view of the actuator 106 of a surgical arm assembly, in accordance with an example of the present disclosure. FIGS. 8A-8C show orientation indicators Proximal and Distal and are discussed below concurrently.

FIG. 8A shows clamps 172, which can be fasteners (such as screws, bolts, rivets, pins, or the like) configured to extend through bores 178 of the bracket 116 to engage the actuator 106 and to secure the actuator with respect to the bracket 116. The bores 178 can be threaded or smooth and the actuator 106 can include features (such as notches or bores) to receive a shank 176 of each clamp 172 therein, In some examples, the clamps 172 can include a head 174 having knurling or ridges for tool-less securing of the clamps 172 to the bracket 116 and a distal portion of the actuator 106.

Figure 8B:
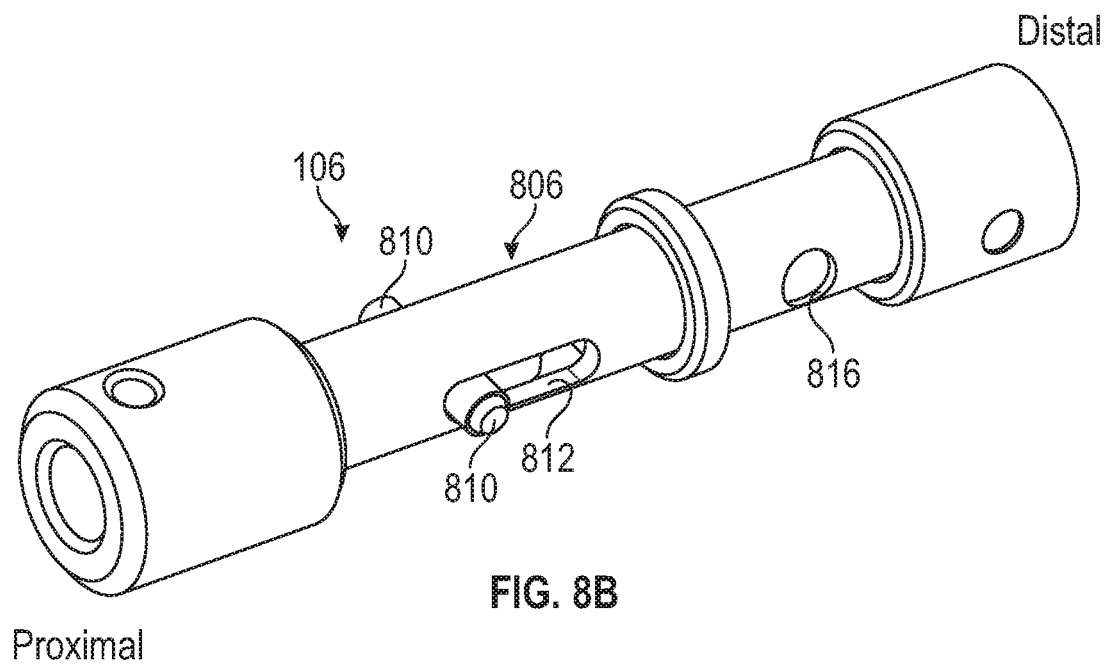
FIG. 8B shows an isometric view of an actuator of a surgical arm assembly, in accordance with an example of the present disclosure.
Figure 8C:
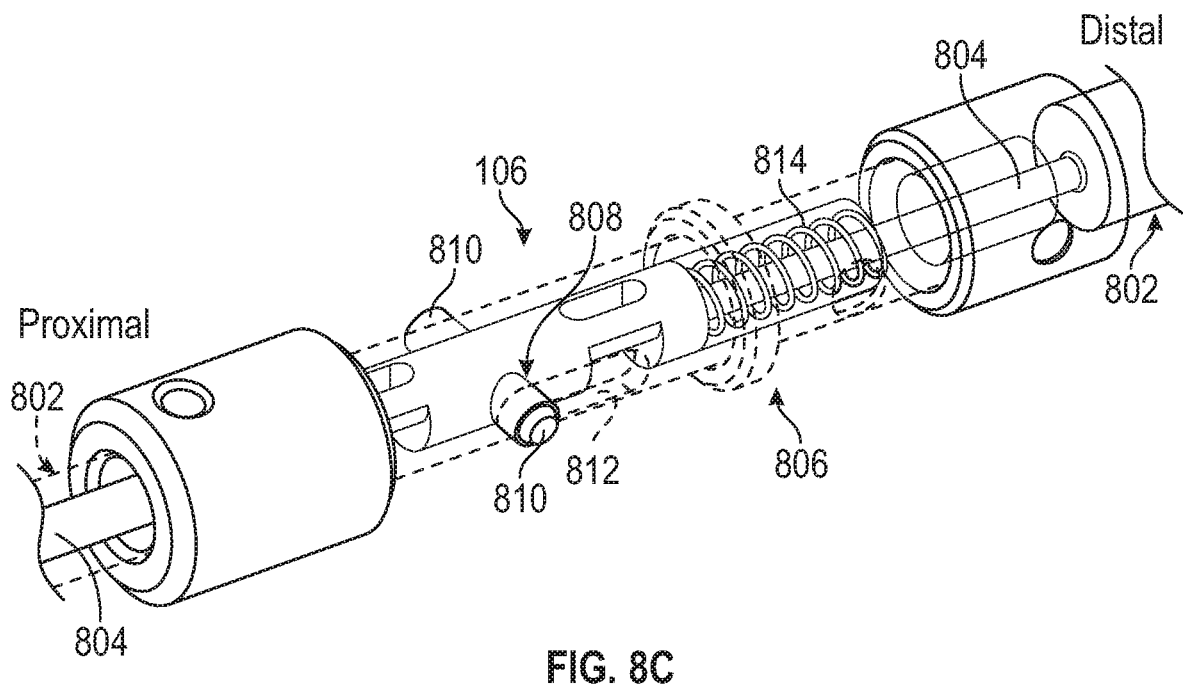
FIG. 8C shows an isometric view of an actuator of a surgical arm assembly, in accordance with an example of the present disclosure.

FIGS. 8B and 8C show the actuator 106 in further detail. The actuator 106 can include a housing 802 that can be securable to a link, a joint, and/or the bracket 116. The actuator 106 can include a cable 804 located within the housing 802, where the cable 804 can be translatable relative to the housing 802. The cable 804 can be located within a body 806 of the actuator 106 and can be connected to a shuttle 808, where the shuttle is located within the body 806.

The shuttle 808 can include bosses 810 (which can be a pin extending through the shuttle 808 in some examples). The bosses 810 can each extend from the shuttle 808 and through channels 812 (respectively) of the body 806. The bosses 810 can be sized and shaped to engage slots of the release 120 (as discussed below with respect to FIG. 9). A biasing element 814 (such as a spring or the like) can be located within the body 806 and can engage the shuttle 808 and the body 806 to bias the shuttle 808 proximally.

In operation, the cable 804 can be moved (by the shuttle 808 via the bosses 810 or by a downstream force), which can cause the bosses 810 to translate proximally to distally within the channels 812 of the body 806 until the bosses contact the body 806 to limit translation of the channel. Movement of the cable 804 can be with respect to the housing 802 and the body 806 and can cause movement of other portions of the cable 804 and other shuttles connected to the cable. When a force is removed from the cable 804 or shuttle 808, the biasing element 814 can cause the shuttle 808 to translate distally within the body 806 until the bosses 810 engage a proximal side of the channels 812.

FIGS. 8B and 8C also show clamp bore 816, which can be configured to receive the shank 176 of the clamp 172 to secure the actuator 106 to the bracket 116.

Figure 9:
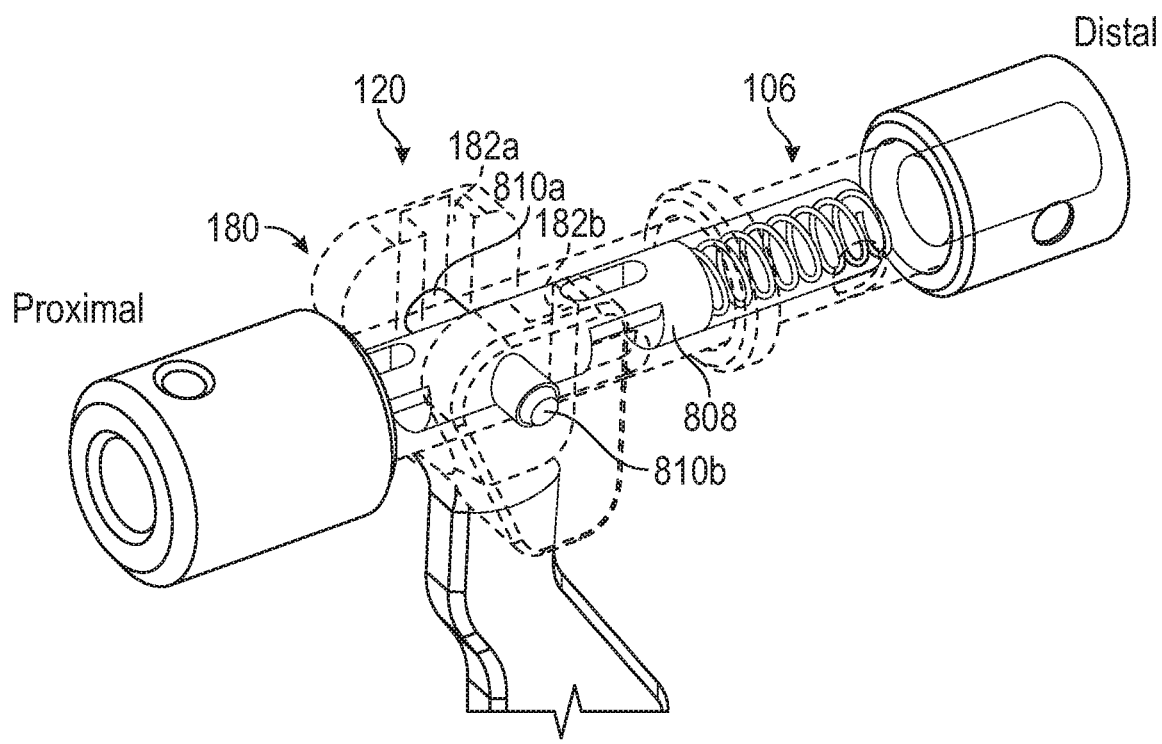
FIG. 9 shows an isometric view of an actuator of a surgical arm assembly, in accordance with an example of the present disclosure.

FIG. 9 shows an isometric view of the actuator 106 and the release 120 of a surgical arm assembly, in accordance with an example of the present disclosure. The components of the actuator 106 and the release 120 are consistent with those discussed above and are discussed in further detail below with respect to FIG. 9.

FIG. 9 shows the release 120 including a receiver 180 where the receiver 180 can include receiver slots 182a and 182b each configured to receive one of the bosses 110a and 110b, respectively. The receiver slots 182a and 182b can limit proximal and distal movement of the bosses with respect to the receiver 180 (and therefore the release 120) to ensure that movement of the bosses 810*a* and 810*b* of the shuttle 808 is transferred to and from the release 120.

Figure 10:
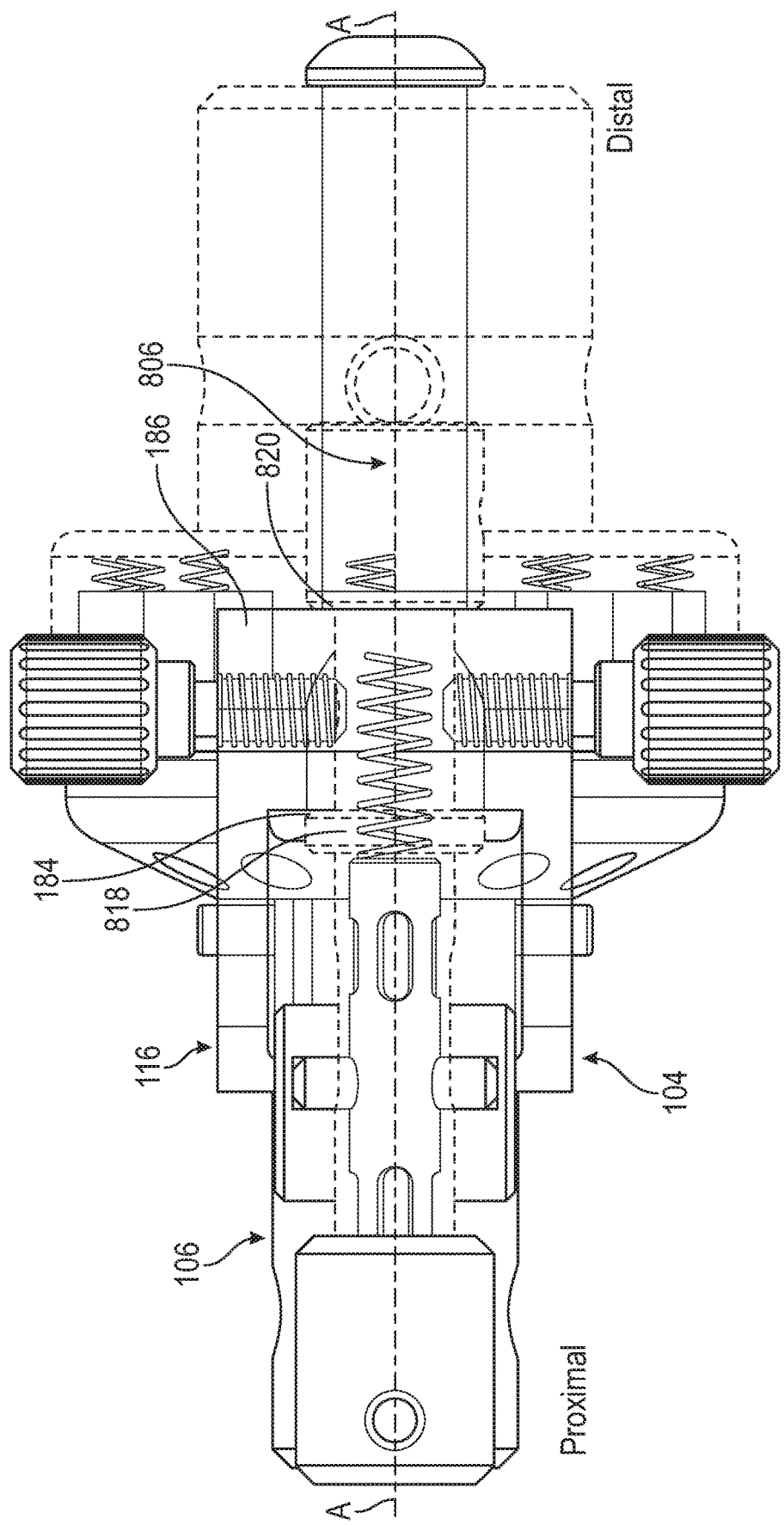
FIG. 10 shows an isometric view of a joint of a surgical arm assembly, in accordance with an example of the present disclosure.
Figure 11:
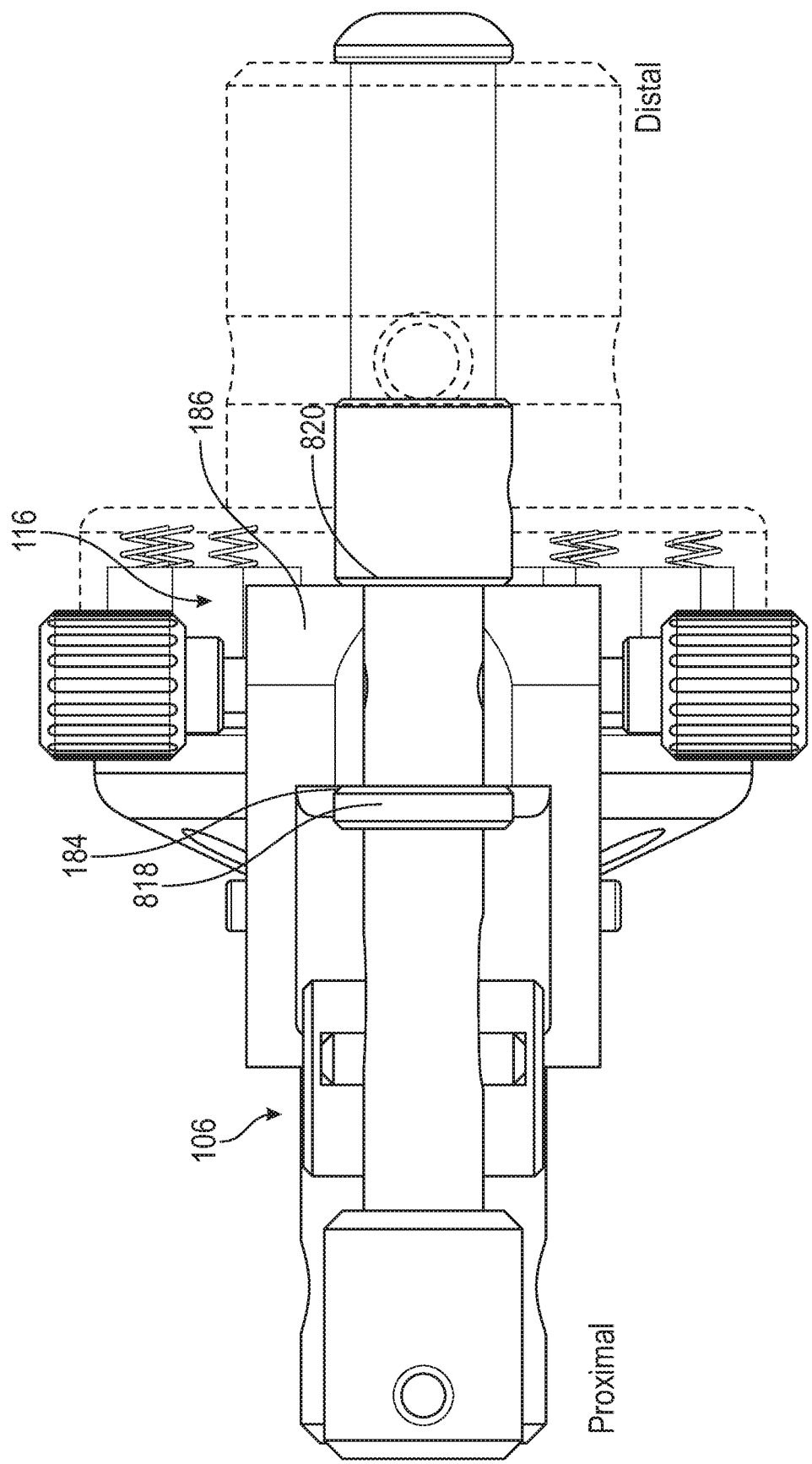
FIG. 11 shows an isometric view of a joint of a surgical arm assembly, in accordance with an example of the present disclosure.
Figure 12:
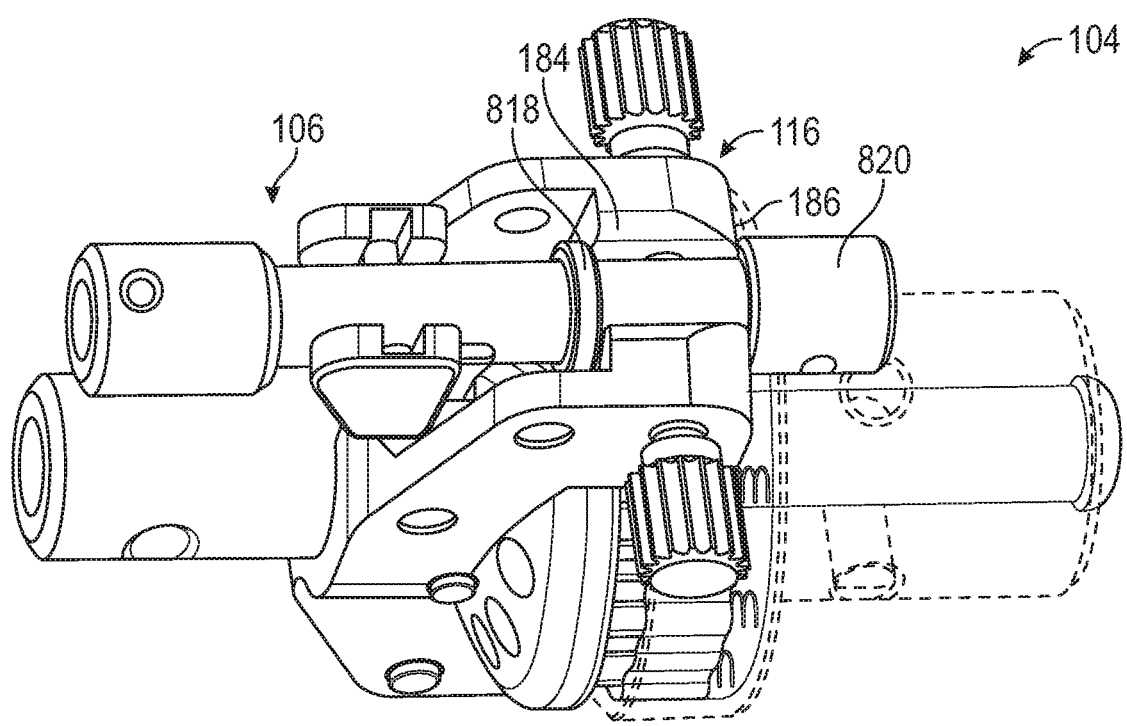
FIG. 12 shows an isometric view of a joint of a surgical arm assembly, in accordance with an example of the present disclosure.

FIG. 10 shows a top view of the joint 104 a surgical arm assembly with the bracket 116 in phantom, in accordance with an example of the present disclosure. FIG. 11 shows a top view of the joint 104 a surgical arm assembly, in accordance with an example of the present disclosure. FIG. 12 shows an isometric view of the joint 104 a surgical arm assembly, in accordance with an example of the present disclosure. FIGS. 10-12 are discussed below concurrently.

The components of the joint 104 and the actuator 106 are consistent with those discussed above and are discussed in further detail below with respect to FIGS. 10-12, which show a proximal flange 818 and a distal flange 820 each of the body 806 of the actuator 106. FIGS. 10-12 further show a proximal portion 184 and a distal portion 186 of the bracket 116, axis A, and orientation indicators Proximal and Distal.

The proximal flange 818 can extend from the body 806 to form a flange or a collar thereof. Similarly, the distal flange 820 can extend from the body 806 to form a flange or a collar thereof with a recess between the proximal flange 818 and the distal flange 820. The proximal portion 184 and the distal portion 186 can be insertable into the recess and can be configured to engage the proximal flange 818 and the distal flange 820 of the body 806 to help limit movement of the body 806 of the actuator 106 with respect to the bracket 116.

Figure 13:
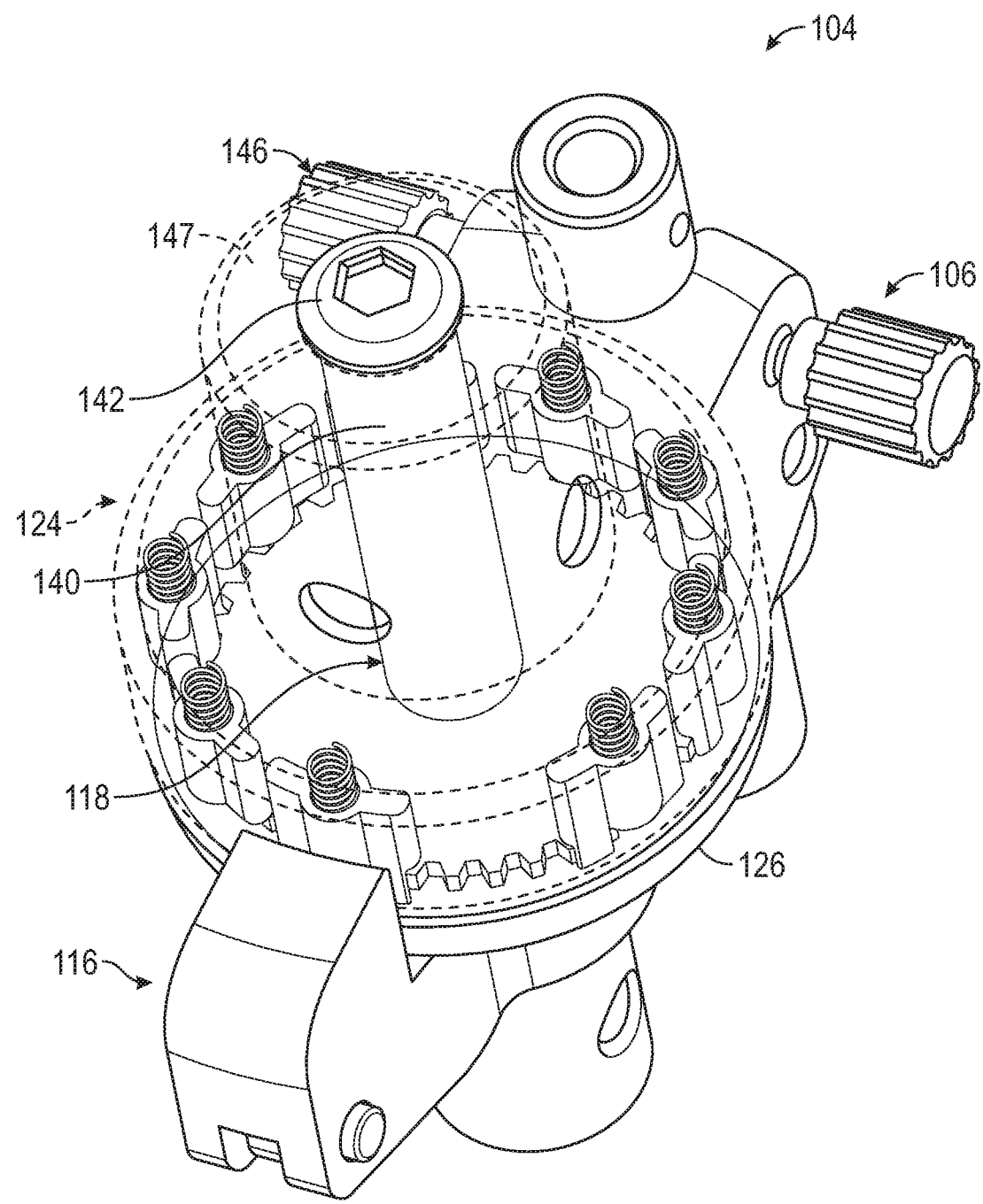
FIG. 13 shows an isometric view of a joint of a surgical arm assembly, in accordance with an example of the present disclosure.

FIG. 13 shows an isometric view of the joint 104 of a surgical arm assembly, in accordance with an example of the present disclosure where the fastener 142 can be a pin, bolt, screw, or the like configured to engage with the extension 140 to secure the distal body portion 146 to the main shaft 118. The fastener 142 can be configured to engage the outer (distal) surface 147 of the meshing gear 124 to retain the meshing gear 124 while allowing rotation of the meshing gear 124 relative to the main shaft 118 and the main gear 122.

Figure 14B:
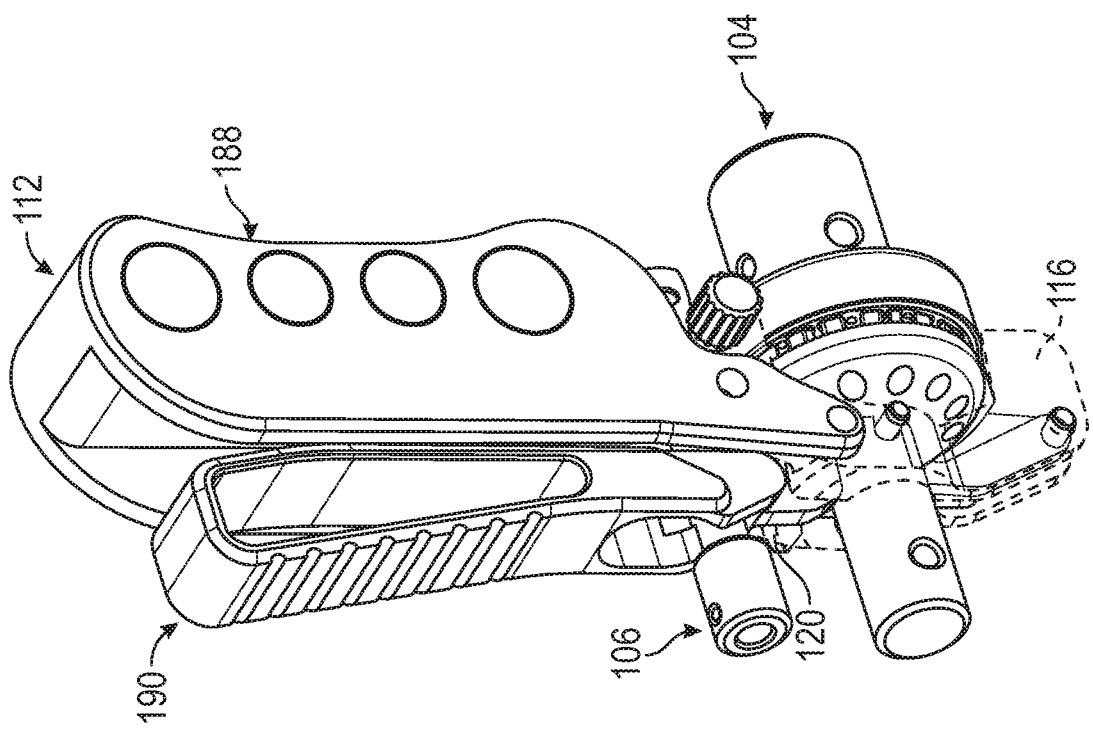
FIG. 14B shows an isometric view of a joint of a surgical arm assembly, in accordance with an example of the present disclosure.
Figure 14A:
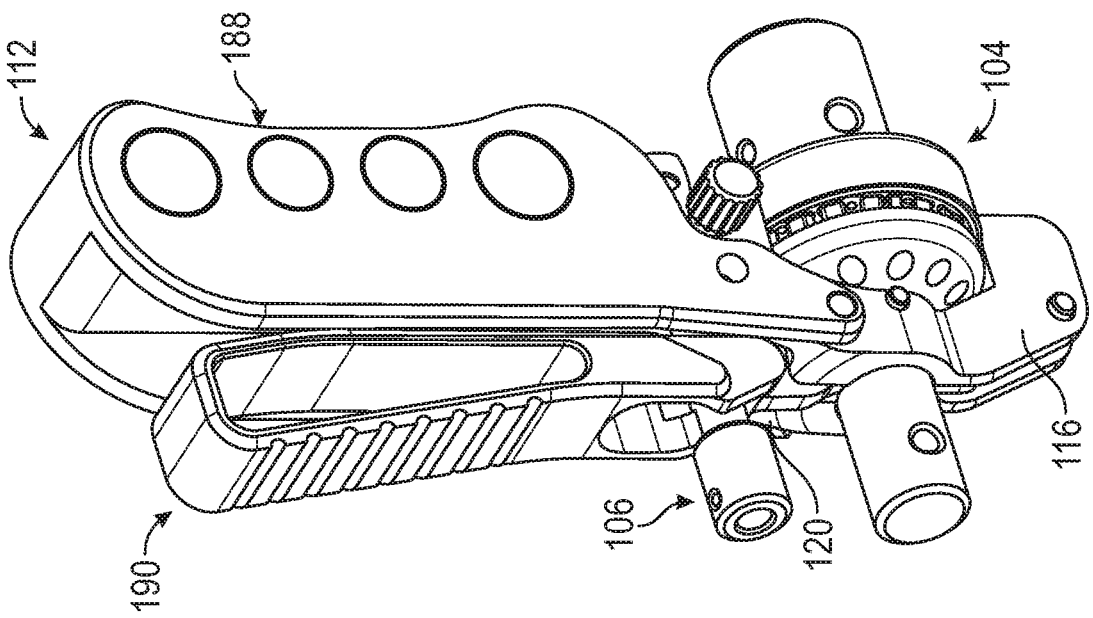
FIG. 14A shows an isometric view of a joint of a surgical arm assembly, in accordance with an example of the present disclosure.

FIG. 14A shows an isometric view of the joint 104, the actuator 106, and the handle assembly 112 of a surgical arm assembly, in accordance with an example of the present disclosure. FIG. 14B shows an isometric view of the joint 104, the actuator 106, and the handle assembly 112 of a surgical arm assembly, with the bracket 116 shown in phantom, in accordance with an example of the present disclosure. FIG. 14C shows a side view of the joint 104, the actuator 106, and the handle assembly 112 of a surgical arm assembly, with the bracket 116 shown in phantom, in accordance with an example of the present disclosure. FIGS. 14A-14C are discussed below concurrently.

As discussed above, the release 120 can be connected to the bracket 116 and can be movable between a locked position and an unlocked position, where the release 120 is configured to engage the release plate 126 to translate the release plate 126 disengage the meshing gear 124 from the main gear 122 when the release 120 is moved from the locked position to the unlocked position. The handle assembly 112 can be coupled to the release 120 and to the bracket 116 to provide ergonomic operability of the release 120.

The handle assembly 112 can include a grip handle 188 that can be connected to the bracket and the handle assembly 112 can include a release handle 190 that can be connected to the release 120, where each of the grip handle 188 and the release handle 190 can be ergonomically shaped. The release handle 190 can be movable with respect to the grip handle 188 and can be operable to move the release 120 between the locked position and the unlocked position to move the shaft pin 160 to engage the release plate 126 to unlock the joint 104.

In some examples, the handle assembly 112 can be adapted to include multiple release handle portions 190, where each portion would control one joint of the mechanical arm assembly 100.

FIG. 15 shows an isometric view of a joint 1504 of a surgical arm assembly 1500, in accordance with an example of the present disclosure. The surgical arm assembly 1500 can include the joint 1504 and an actuator 1506. The joint 1504 can include a bracket 1516, a main shaft 1518, a meshing gear 1524, and a release plate 1526. Also shown in FIG. 15 are axis A and orientation indicators Proximal and Distal.

The components of the joint 1504 can be similar to those of the joint 104 discussed above, except that the meshing gear 1524 can include a meshing gear plate (or sprung gear) configured to move the teeth of the meshing gear 1524 in unison to engage the main gear. Any of the joints discussed above or below can be modified to include such a meshing gear. Further details are discussed below with respect to FIGS. 16A-18.

Figure 16A:
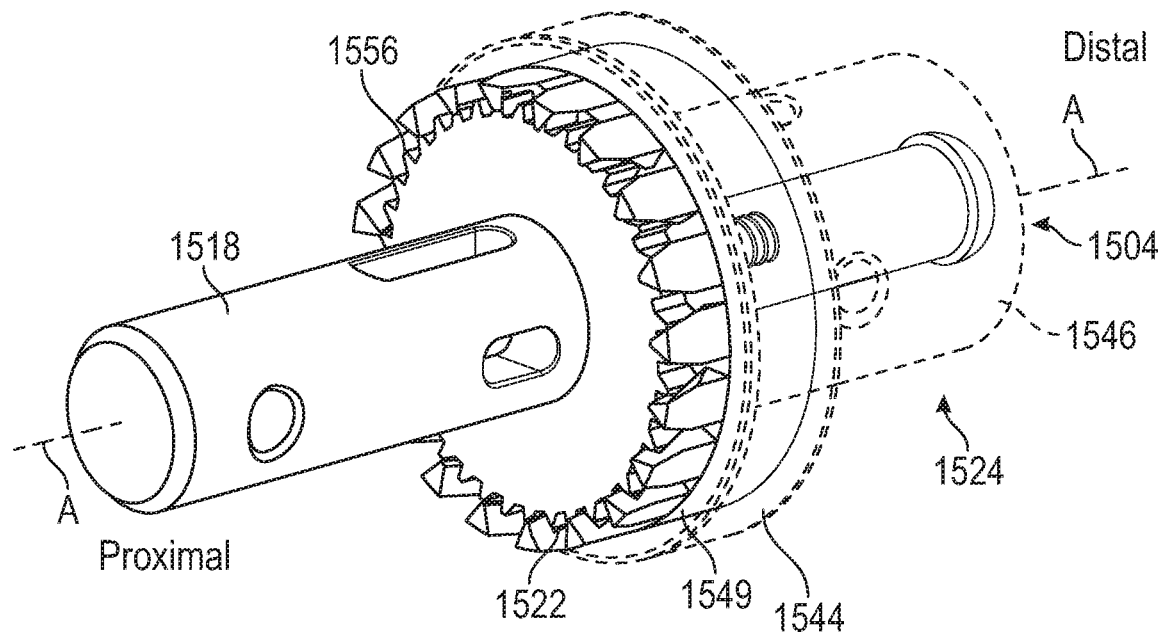
FIG. 16A shows an isometric view of a portion of a joint of a surgical arm assembly, in accordance with an example of the present disclosure.
Figure 16B:
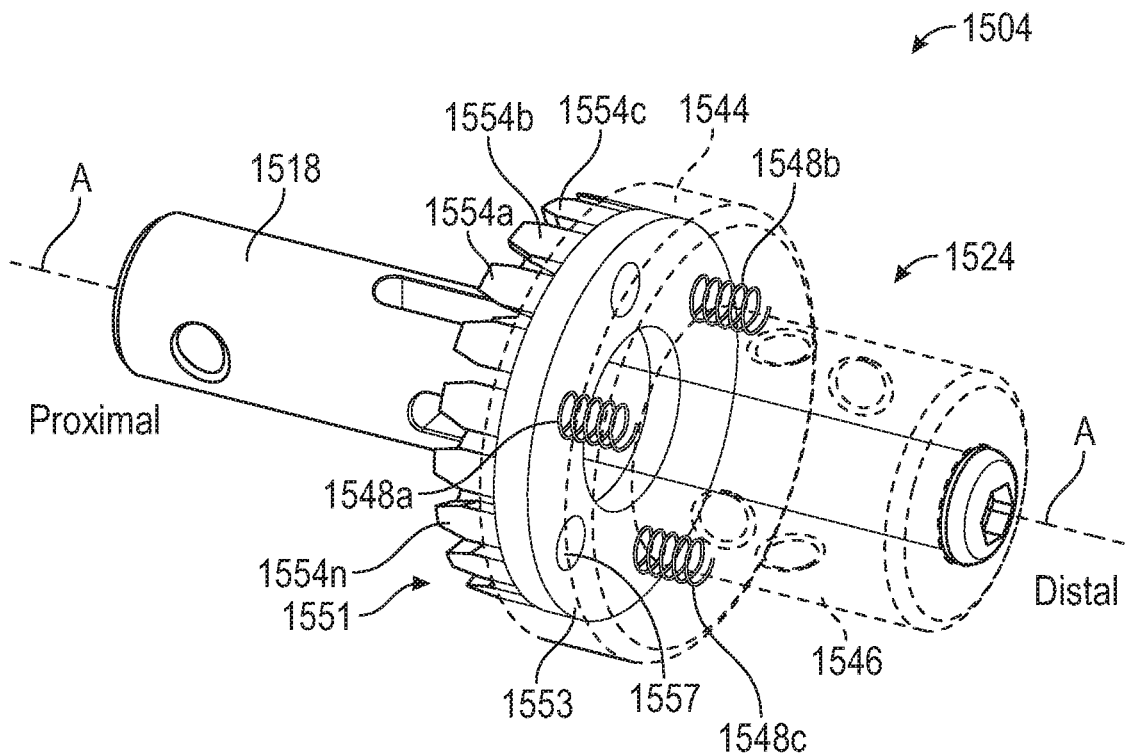
FIG. 16B shows an isometric view of a portion of a joint of a surgical arm assembly, in accordance with an example of the present disclosure.
Figure 18:
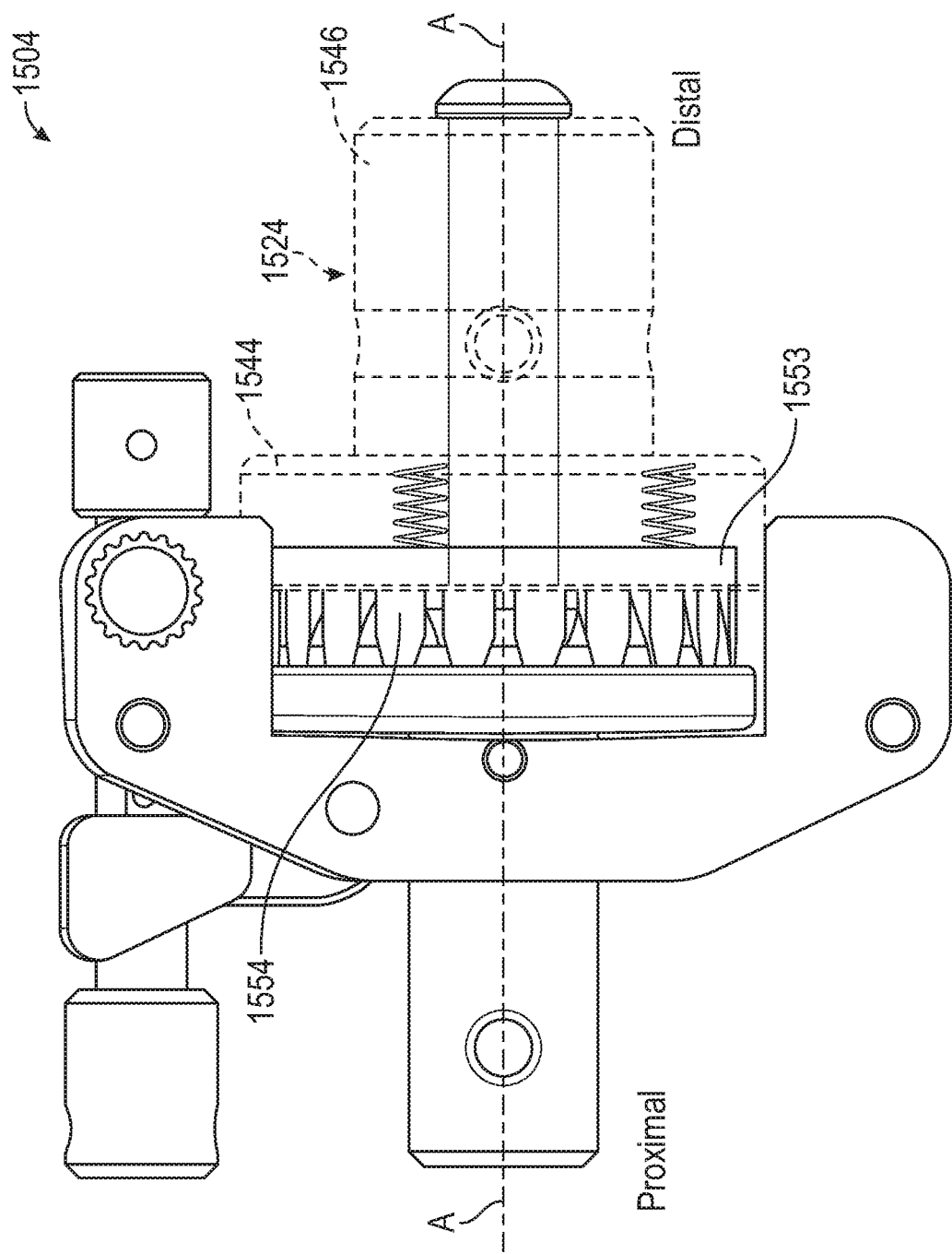
FIG. 18 shows an isometric view of a joint of a surgical arm assembly, in accordance with an example of the present disclosure.

FIG. 16A shows an isometric view of a portion of the joint 1504 of a surgical arm assembly, in accordance with an example of the present disclosure. FIG. 16B shows an isometric view of a portion of the joint 1504 of a surgical arm assembly, in accordance with an example of the present disclosure. FIG. 17A shows an isometric view of a portion of the joint 1504 of a surgical arm assembly, in accordance with an example of the present disclosure. FIG. 17B shows an isometric view of a portion of the joint 1504 of a surgical arm assembly, in accordance with an example of the present disclosure. FIG. 18 shows an isometric view of the joint 1504 of a surgical arm assembly, in accordance with an example of the present disclosure.

FIGS. 16A-16B show the main gear 1522 and the meshing gear 1524. The meshing gear 1524 can include proximal body portion 1544, a distal body portion 1546, biasing elements 1548*a*-1548*c*, and a sprung gear 1551. The sprung gear 1551 can include a base 1553 and teeth 1554*a*-1554*n* (collectively referred to as teeth 1554).

The base 1553 can be a plate having a disk-shape in some examples and can have other shapes in other examples. The base 1553 can be sized to be located in a base bore 1549 of the proximal body portion 1544 of the meshing gear 1524. The teeth 1554 can extend proximally from the base 1553 around a periphery of the base 1553 and the teeth 1554 can be configured to engage the teeth 1556 of the main gear 1522 to couple the main gear 1522 to the meshing gear 1524. The teeth 1554 can be sized and shaped to engage the teeth 1556 and can be of any number equal to or less than the number of main gear teeth 1556.

FIG. 16B also shows the biasing elements 1548 located within the base bore 1549 to engage the proximal body portion 1544 and the base 1553 to bias the teeth 1553 of the sprung gear 1551 to extend from the base bore 1549 to engage the teeth 1556 of the main gear 1522.

FIG. 17B further shows that the proximal body portion 1544 can include bosses 1555*a*-1555*c* (collectively referred to as bosses 1555) which can be configured to insert into bores 1557 (shown in FIG. 16B) of the base 1553 of the sprung gear 1551. The bosses 1555 can engage the base 1553 to limit relative rotation of the sprung gear 1551 with respect to the proximal portion 1544 of the meshing gear 1524. Such a sprung gear can include fewer parts and can therefore reduce manufacturing costs.

Figure 19:
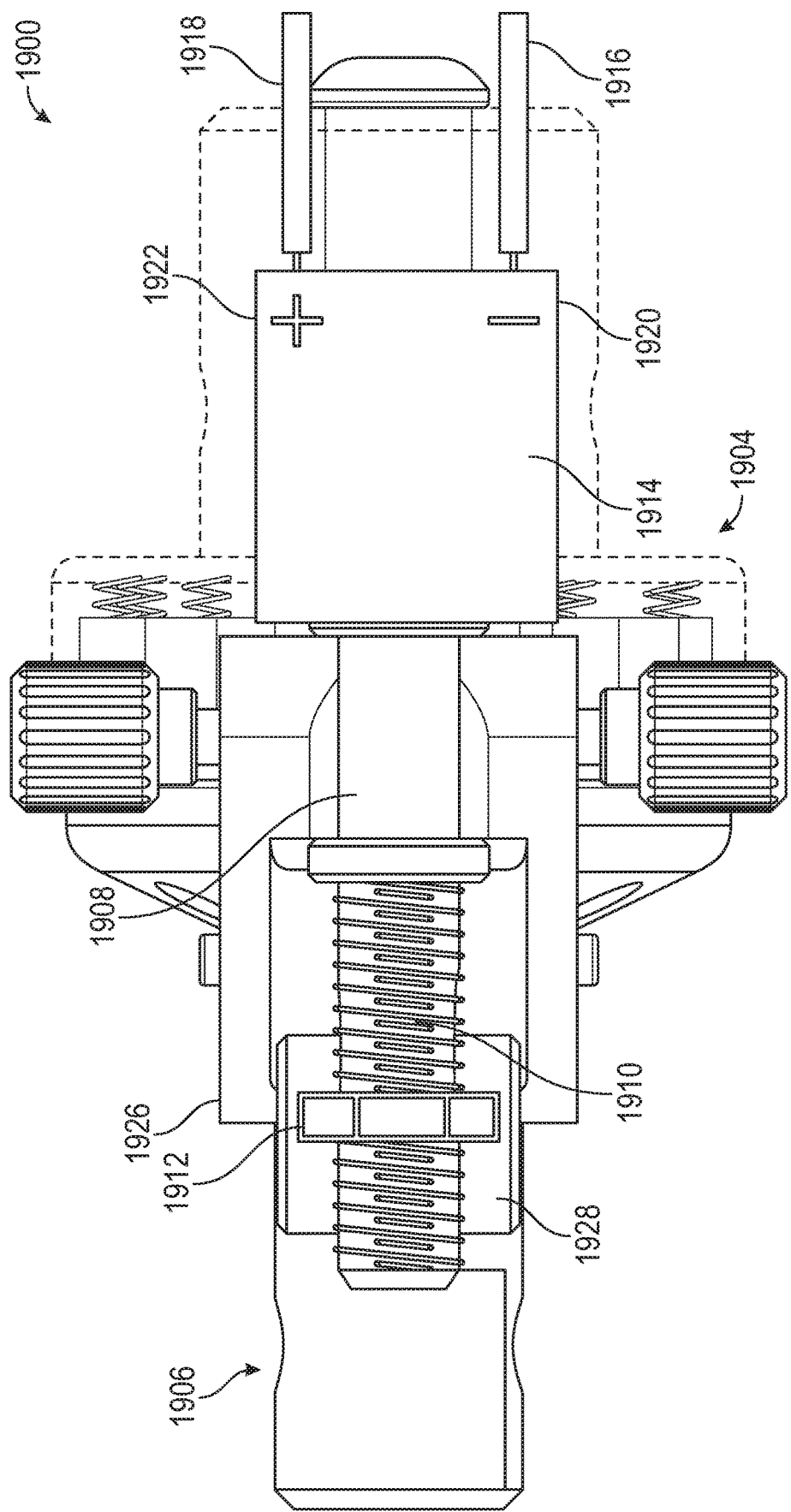
FIG. 19 shows an isometric view of a joint of a surgical arm assembly, in accordance with an example of the present disclosure.

FIG. 19 shows an isometric view of a joint 1904 of a surgical arm assembly 1900, in accordance with an example of the present disclosure. The surgical arm assembly 1900 can include an electric actuator that can be used to electrically operate the actuator of the arm. Any of the arms discussed above or below can be modified to include an electric actuator.

The surgical arm assembly 1900 can include the joint 1904 and the actuator 1906, where the actuator 1906 can include a shaft 1908 (including a threaded portion 1910), a fastener 1912, a motor 1914, a negative lead 1916, and a positive lead 1918. The motor 1914 can include a negative terminal 1920 and a positive terminal 1922.

The shaft 1908 of the actuator 1906 can be secured to a bracket 1926 of the joint 1904 and the fastener 1912 can be secured to a release 1928 of the joint 1904. The fastener 1912 can be further secured to the threaded portion 1910 of the shaft 1908 to secure the actuator 1906 to the release 1920.

The motor 1914 can be a rotating electric motor connected to the sleeve 1908. The sleeve 1908 can receive the threaded portion therethrough and the sleeve can be secured to the motor 1914 using mounting features of the motor 1914 and the sleeve 1908, such as fasteners. Thumb screws can secure the sleeve 1908 to the bracket 1926 to prevent relative movement of the sleeve 1908 with respect to the motor 1914. A shaft of the motor (not visible in FIG. 19) can be coupled to the threaded portion 1910 and can be driven by the motor 1914 to rotate within the sleeve 1908 and with respect to the bracket 1926. Rotation of the shaft can cause rotation of the threaded portion 1910 such that the threaded portion 1910 can thread into and out of the fastener 1912 causing the fastener 1912 (and the release 1928 connected thereto) to move with respect to the bracket 1926 to lock and unlock the gears of the joint 1904. In some examples, a switch or a button can be operated by a user to control a direction of rotation of the motor 1914 and therefore to control locking and unlocking of the joint 1904.

In some examples, a switch can be provided at the distal-most joint to control operation of each of the motors for each joint simultaneously to lock and unlock the joints together. In this and other examples, individual switches can be provided at the distal-most joint for independent joint locking and unlocking joints from the same location.

The motor arrangement can be supplied sterile for connection to a mechanical arm assembly and the motor and cable assembly can be disposable. In some examples, the motor can be autoclavable, for example, where the components of the motor are sealed and able to withstand high external temperatures.

In some examples, each motors of each joint can be wirelessly controlled via, for example, a blue tooth control devices such as a button or switch mounted, for example, on a distal portion of the mechanical arm assembly.

Though the motor 1914 is discussed as being rotational, the motor 1914 can be a liner motor (such as a solenoid) in other examples where the shaft 1908 can be integral with or connected to the motor 1914. A surgical arm 1900 can include multiple joints having multiple actuators with motors that can be wired in series to simultaneously lock and unlock all of the joints, or that can be wired in parallel to lock and unlock all of the joints independently of each other.

EXAMPLES

The following, non-limiting examples, detail certain aspects of the present subject matter to solve the challenges and provide the benefits discussed herein, among others.

Example 1 is a mechanical arm assembly comprising: a link movable in space; an actuator including a housing secured to the link, the actuator including a cable within the housing, the cable translatable relative to the housing and the link; and a joint comprising: a main shaft extending along a longitudinal axis; a main gear coupled to the main shaft, the main gear including a plurality of main gear teeth extending radially outward from a periphery of the main gear and rotatable about the longitudinal axis; a meshing gear in coaxial alignment with the main gear and rotatable about the longitudinal axis, the meshing gear comprising: a meshing gear tooth set releasably engageable with the main gear teeth; a bore configured to receive the meshing gear tooth set therein; and a biasing element disposable in the bore to engage the meshing gear tooth set to bias the meshing gear tooth set to extend from the meshing gear; and a release plate supported by the main shaft and translatable in response to movement of the actuator to contact the meshing gear tooth set, thereby disengaging the meshing gear tooth set from the main gear teeth to allow rotation of the meshing gear relative to the main gear.

In Example 2, the subject matter of Example 1 optionally includes wherein the main shaft includes an extension extending through the meshing gear, and the joint further comprises a fastener securable to the main shaft to engage an outer surface of the meshing gear to retain the meshing gear while allowing rotation of the meshing gear relative to the main shaft and the main gear.

In Example 3, the subject matter of any one or more of Examples 1-2 optionally include wherein the meshing gear tooth set includes a base disposable in the bore and includes a first tooth and a second tooth coupled to the base each of the first tooth and the second tooth extending away from the bore.

In Example 4, the subject matter of Example 3 optionally includes wherein the first tooth and the second tooth have a truncated triangular pyramid shape.

In Example 5, the subject matter of Example 4 optionally includes wherein the first tooth and the second tooth are tapered as the first tooth and the second tooth extend from the base.

In Example 6, the subject matter of Example 5 optionally includes wherein the first tooth is spaced apart from the second tooth by a distance substantially equal to a width of the first tooth.

In Example 7, the subject matter of Example 6 optionally includes wherein the meshing gear includes a second bore circumferentially spaced away from the bore, includes a second tooth set disposable in the second bore, and includes a second biasing element disposable in the second bore to engage the second tooth set to bias the second tooth set away from the second bore, the second tooth set configured to be engaged by the release plate to translate the second tooth set into the second bore to disengage the second tooth set from the main gear teeth.

In Example 8, the subject matter of Example 7 optionally includes wherein the second tooth set includes a second base disposable in the second bore and includes a third tooth and a fourth tooth coupled to the second base and each extending away from the second bore.

In Example 9, the subject matter of Example 8 optionally includes wherein the bore and the second bore are circumferentially spaced with respect to the meshing gear such that the first tooth and the second tooth are spaced from each other at a first angle and the third tooth and the fourth tooth are spaced from each other at the first angle and the second tooth and the third tooth are spaced from each other at a second angle greater than the first angle such that when the first tooth and the second tooth align with the main gear teeth the third tooth and the fourth tooth do not align with the main gear teeth.

In Example 10, the subject matter of Example 9 optionally includes/nMT)/i, where nMT is a number of main gear teeth and i is an increment of adjustment of the meshing gear with respect to the main gear.

In Example 11, the subject matter of any one or more of Examples 1-10 optionally include a bracket connected to the main shaft; and a release connected to the bracket and movable between a locked position and an unlocked position, the release configured to engage the release plate to translate the release plate to engage the tooth set to disengage the meshing gear from the main gear when the release is moved from the locked position to the unlocked position.

In Example 12, the subject matter of Example 11 optionally includes wherein the main shaft includes a release slot extending through the main shaft configured to receive the release therethrough and the main shaft includes a pin slot extending through the main shaft substantially orthogonally to the release slot, wherein the release includes a handle pin bore extending therethrough, and wherein the joint includes a first pin insertable through the pin slot and the handle pin bore to couple the main shaft to the release, the first pin translatable within the pin slot to limit translation of the release with respect to the main shaft.

In Example 13, the subject matter of Example 12 optionally includes wherein the bracket includes a first bracket pin bore and a second bracket pin bore spaced away from the first bracket pin bore, wherein the release includes a second handle pin bore spaced away from the handle pin bore, the first bracket pin bore configured to receive the first pin therethrough to secure the handle to the bracket, the second bracket pin bore and the second handle pin bore configured to receive a second pin therethrough to create a pivot point for the release to pivot with respect to the bracket.

In Example 14, the subject matter of Example 13 optionally includes an actuator connected to the release and operable to rotate the handle about the pivot point.

In Example 15, the subject matter of any one or more of Examples 1-14 optionally include wherein the release includes a pair of opposing channels and wherein the actuator includes a pair of opposing pins disposable within the pair of opposing channels to couple the release to the actuator.

In Example 16, the subject matter of any one or more of Examples 1-15 optionally include wherein the bracket includes a pair of opposing flanges configured to engage the actuator to limit movement of the actuator with respect to the bracket, and wherein the joint includes an actuator fastener securable to the pair of opposing flanges and to the actuator to limit movement of the actuator with respect to the bracket.

Example 17 is a mechanical articulable surgical arm assembly comprising: a link movable in space; an actuator including a housing secured to the link, the actuator including a cable within the housing, the cable translatable relative to the housing and the link; and a joint coupled to the link, the joint comprising: a main shaft extending along a longitudinal axis, the main shaft coupled to the link; a main gear coupled to the main shaft and extending outward from the main shaft, the main gear including a plurality of main gear teeth extending radially outward from a periphery of the main gear; a meshing gear in coaxial alignment with the main gear, the meshing gear comprising: a meshing gear tooth releasably engageable with the main gear teeth; a bore configured to receive the meshing gear tooth therein; and a biasing element disposable in the bore to engage the meshing gear tooth to bias the meshing gear tooth to extend from the meshing gear; and a release plate supported by the main shaft and translatable in response to movement of the actuator to engage the meshing gear tooth to disengage the meshing gear tooth from the main gear teeth to allow the meshing gear to rotate relative to the main gear.

In Example 18, the subject matter of Example 17 optionally includes a second link connected to the meshing gear and rotatable with the meshing gear relative to the first link and relative to the main shaft when the release plate engages the meshing gear tooth to disengage the meshing gear tooth from the main gear teeth.

In Example 19, the subject matter of any one or more of Examples 17-18 optionally include a bracket connected to the main shaft; and a release connected to the bracket and movable between a locked position and an unlocked position, the release configured to engage the release plate to translate the release plate to engage the tooth to disengage the meshing gear from the main gear when the release is moved from the locked position to the unlocked position.

In Example 20, the subject matter of Example 19 optionally includes a grip handle connected to the bracket; and a release handle connected to the release, the release handle operable to move the release between the locked position and the unlocked position.

In Example 21, the subject matter of any one or more of Examples 17-20 optionally include a tool holder connected to the meshing gear and rotatable with the meshing gear relative to the first link and the main shaft when the release plate engages the meshing gear tooth to disengage the meshing gear tooth from the main gear teeth, the tool holder configured to support a surgical tool.

Example 22 is a surgical arm assembly comprising: a link movable in space; an actuator including a housing secured to the link, the actuator including a cable within the housing, the cable translatable relative to the housing and the link, the actuator movable between a locked position and an unlocked position; and a first joint and a second joint, each movable between locked and unlocked positions, each of the first joint and the second joint comprising: a main shaft extending along a longitudinal axis; a main gear coupled to the main shaft and extending outward from the main shaft, the main gear including a plurality of main gear teeth extending radially outward from a periphery of the main gear; a meshing gear in coaxial alignment with the main gear, the meshing gear comprising: a plurality of meshing gear tooth sets engageable with the main gear; a plurality of teeth bores, each of the plurality of teeth bores configured to receive one of the plurality of meshing gear tooth sets therein; and a plurality of biasing elements each disposable in one of the plurality of teeth bores to engage one of the plurality of meshing gear tooth sets to bias the plurality of meshing gear tooth sets to extend from the meshing gear; and a release plate supported by the main shaft and translatable in response to movement of the actuator toward the unlocked position to engage the plurality of meshing gear tooth sets to disengage the plurality of meshing gear tooth sets from the plurality of main gear teeth to allow the meshing gear to rotate relative to the main gear.

In Example 23, the subject matter of Example 22 optionally includes a second link connected to the meshing gear of the first joint at a distal portion of the second link and connected to the main shaft of the second joint at a proximal portion of the second link; wherein movement of the actuator toward the unlocked position moves the cable to unlock both the first joint and the second joint and movement of the actuator toward the lock position moves the cable to lock both the first joint and the second joint.

In Example 24, the subject matter of Example 23 optionally includes wherein the first lock and the second lock are independently operable to move between the locked position and the unlocked position.

In Example 25, the system, device, or method of any one of or any combination of Examples 1-24 is optionally configured such that all elements or options recited are available to use or select from.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A mechanical arm assembly comprising:
    a link movable in space;
    an actuator including a housing secured to the link, the actuator including a cable within the housing, the cable translatable relative to the housing and the link; and
    a joint comprising:
        a main shaft extending along a longitudinal axis;
        a main gear coupled to the main shaft, the main gear including a plurality of main gear teeth extending radially outward from a periphery of the main gear and rotatable about the longitudinal axis;
        a meshing gear in coaxial alignment with the main gear and rotatable about the longitudinal axis, the meshing gear comprising:
            a meshing gear tooth set releasably engageable with the main gear teeth;
            a bore configured to receive the meshing gear tooth set therein; and
            a biasing element disposable in the bore to engage the meshing gear tooth set to bias the meshing gear tooth set to extend from the meshing gear; and
        a release plate supported by the main shaft and translatable in response to movement of the actuator to contact the meshing gear tooth set, thereby disengaging the meshing gear tooth set from the main gear teeth to allow rotation of the meshing gear relative to the main gear.

2. The assembly of claim 1, wherein the main shaft includes an extension extending through the meshing gear, and the joint further comprises a fastener securable to the main shaft to engage an outer surface of the meshing gear to retain the meshing gear while allowing rotation of the meshing gear relative to the main shaft and the main gear.

3. The assembly of claim 1, wherein the meshing gear tooth set includes a base disposable in the bore and includes a first tooth and a second tooth coupled to the base each of the first tooth and the second tooth extending away from the bore.

4. The assembly of claim 3, wherein the first tooth and the second tooth have a truncated triangular pyramid shape.

5. The assembly of claim 4, wherein the first tooth and the second tooth are tapered as the first tooth and the second tooth extend from the base.

6. The assembly of claim 5, wherein the first tooth is spaced apart from the second tooth by a distance substantially equal to a width of the first tooth.

7. The assembly of claim 6, wherein the meshing gear includes a second bore circumferentially spaced away from the bore, includes a second tooth set disposable in the second bore, and includes a second biasing element disposable in the second bore to engage the second tooth set to bias the second tooth set away from the second bore, the second tooth set configured to be engaged by the release plate to translate the second tooth set into the second bore to disengage the second tooth set from the main gear teeth.

8. The assembly of claim 7, wherein the second tooth set includes a second base disposable in the second bore and includes a third tooth and a fourth tooth coupled to the second base and each extending away from the second bore.

9. The assembly of claim 8, wherein the bore and the second bore are circumferentially spaced with respect to the meshing gear such that the first tooth and the second tooth are spaced from each other at a first angle and the third tooth and the fourth tooth are spaced from each other at the first angle and the second tooth and the third tooth are spaced from each other at a second angle greater than the first angle such that when the first tooth and the second tooth align with the main gear teeth the third tooth and the fourth tooth do not align with the main gear teeth.

10. The assembly of claim 9, wherein a number of meshing gear teeth is equal to or greater than (360/nMT)/i, where nMT is a number of main gear teeth and i is an increment of adjustment of the meshing gear with respect to the main gear.

11. The assembly of claim 1, further comprising:
a bracket connected to the main shaft; and
a release connected to the bracket and movable between a locked position and an unlocked position, the release configured to engage the release plate to translate the release plate to engage the tooth set to disengage the meshing gear from the main gear when the release is moved from the locked position to the unlocked position.

12. The assembly of claim 11, wherein the main shaft includes a release slot extending through the main shaft configured to receive the release therethrough and the main shaft includes a pin slot extending through the main shaft substantially orthogonally to the release slot, wherein the release includes a handle pin bore extending therethrough, and wherein the joint includes a first pin insertable through the pin slot and the handle pin bore to couple the main shaft to the release, the first pin translatable within the pin slot to limit translation of the release with respect to the main shaft.

13. The assembly of claim 12, wherein the bracket includes a first bracket pin bore and a second bracket pin bore spaced away from the first bracket pin bore, wherein the release includes a second handle pin bore spaced away from the handle pin bore, the first bracket pin bore configured to receive the first pin therethrough to secure the handle to the bracket, the second bracket pin bore and the second handle pin bore configured to receive a second pin therethrough to create a pivot point for the release to pivot with respect to the bracket.

14. The assembly of claim 13, further comprising:
an actuator connected to the release and operable to rotate t handle about the pivot point.

15. The assembly of claim 1, wherein the release includes a pair of opposing channels and wherein the actuator includes a pair of opposing pins disposable within the pair of opposing channels to couple the release to the actuator.

16. The assembly of claim 1, wherein the bracket includes a pair of opposing flanges configured to engage the actuator to limit movement of the actuator with respect to the bracket, and wherein the joint includes an actuator fastener securable to the pair of opposing flanges and to the actuator to limit movement of the actuator with respect to the bracket.

17. A mechanical articulable surgical arm assembly comprising:
a link movable in space;
an actuator including a housing secured to the link, the actuator including a cable within the housing, the cable translatable relative to the housing and the link; and
a joint coupled to the link, the joint comprising:
a main shaft extending along a longitudinal axis, the main shaft coupled to the link;
a main gear coupled to the main shaft and extending outward from the main shaft, the main gear including a plurality of main gear teeth extending radially outward from a periphery of the main gear;
a meshing gear in coaxial alignment with the main gear, the meshing gear comprising:
a meshing gear tooth releasably engageable with the main gear teeth;
a bore configured to receive the meshing gear tooth therein; and
a biasing element disposable in the bore to engage the meshing gear tooth to bias the meshing gear tooth to extend from the meshing gear; and
a release plate supported by the main shaft and translatable in response to movement of the actuator to engage the meshing gear tooth to disengage the meshing gear tooth from the main gear teeth to allow the meshing gear to rotate relative to the main gear.

18. The assembly of claim 17, further comprising:
a second link connected to the meshing gear and rotatable with the meshing gear relative to the first link and relative to the main shaft when the release plate engages the meshing gear tooth to disengage the meshing gear tooth from the main gear teeth.

19. The assembly of claim 17, further comprising:
a bracket connected to the main shaft; and
a release connected to the bracket and movable between a locked position and an unlocked position, the release configured to engage the release plate to translate the release plate to engage the tooth to disengage the meshing gear from the main gear when the release is moved from the locked position to the unlocked position.

20. The assembly of claim 19, further comprising:
a grip handle connected to the bracket; and
a release handle connected to the release, the release handle operable to move the release between the locked position and the unlocked position.

21. The assembly of claim 17, further comprising:
a tool holder connected to the meshing gear and rotatable with the meshing gear relative to the first link and the main shaft when the release plate engages the meshing gear tooth to disengage the meshing gear tooth from the main gear teeth, the toot holder configured to support a surgical tool.

22. A surgical arm assembly comprising:
a link movable in space;
an actuator including a housing secured to the link, the actuator including a cable within the housing, the cable translatable relative to the housing and the link, the actuator movable between a locked position and an unlocked position; and
a first joint and a second joint, each movable between locked and unlocked positions, each of the first joint and the second joint comprising:
a main shaft extending along a longitudinal axis;
a main gear coupled to the main shaft and extending outward from the main shaft, the main gear including a plurality of main gear teeth extending radially outward from a periphery of the main gear;
a meshing gear in coaxial alignment with the main gear, the meshing gear comprising:
a plurality of meshing gear tooth sets engageable with the main gear;
a plurality of teeth bores, each of the plurality of teeth bores configured to receive one of the plurality of meshing gear tooth sets therein; and
a plurality of biasing elements each disposable in one of the plurality of teeth bores to engage one of the plurality of meshing gear tooth sets to bias the plurality of meshing gear tooth sets to extend from the meshing gear; and a release plate supported by the main shaft and translatable in response to movement of the actuator toward the unlocked position to engage the plurality of meshing gear tooth sets to disengage the plurality of meshing gear tooth sets from the plurality of main gear teeth to allow the meshing gear to rotate relative to the main gear.

23. The assembly of claim 22, further comprising:

a second link connected to the meshing gear of the first joint at a distal portion of the second link and connected to the main shaft of the second joint at a proximal portion of the second link;

wherein movement of the actuator toward the unlocked position moves the cable to unlock both the first joint and the second joint and movement of the actuator toward the lock position moves the cable to lock both the first joint and the second joint.

24. The assembly of claim 23, further comprising:

wherein the first lock and the second lock are independently operable to move between the locked position and the unlocked position.

* * * * *

UNITED STATES PATENT AND TRADEMARK OFFICE
CERTIFICATE OF CORRECTION

PATENT NO. : 11,517,396 B2
APPLICATION NO. : 16/802166
DATED : December 6, 2022
INVENTOR(S) : Saddy Garcia It is certified that error appears in the above-identified patent and that said Letters Patent is hereby corrected as shown below:

In the Claims

In Column 21, Line 44, in Claim 14, delete "t" and insert --the-- therefor

In Column 22, Line 42, in Claim 21, delete "toot" and insert --tool-- therefor

Signed and Sealed this
Fourth Day of April, 2023

Katherine Kelly Vidal
*Director of the United States Patent and Trademark Office*